(12) United States Patent
Tseng et al.

(10) Patent No.: US 8,518,393 B2
(45) Date of Patent: Aug. 27, 2013

(54) FUNGI TRANSFORMANT FOR MELANIN PRODUCTION AND USES THEREOF

(75) Inventors: Min-Nan Tseng, Changzhi Township, Pingtung County (TW); Shean-Shong Tzean, Taipei (TW)

(73) Assignees: Kaohsiung District Agricultral Research and Extension Station, COA, EY, Pingtung County (TW); National Taiwan University, Taipei (TW)

( * ) Notice: Subject to any disclaimer, the term of this patent is extended or adjusted under 35 U.S.C. 154(b) by 175 days.

(21) Appl. No.: 12/954,768

(22) Filed: Nov. 26, 2010

(65) Prior Publication Data

US 2011/0158970 A1     Jun. 30, 2011

(30) Foreign Application Priority Data

Dec. 31, 2009   (TW) .............................. 98146417 A

(51) Int. Cl.
*A61B 5/055*     (2006.01)
*A61K 49/00*     (2006.01)
(52) U.S. Cl.
USPC ...................................... 424/93.5; 424/93.21

(58) Field of Classification Search
None
See application file for complete search history.

(56) References Cited

PUBLICATIONS

Tseng, et al. (Jul. 2011) "Enhancing the Stress Tolerance and Virulence of an Entomopathogen by Metabolic Engineering of Dihydroxynaphthalene Melanin Biosynthesis Genes", Applied and Environmental Microbiology, 77(13): 4508-19.*

* cited by examiner

*Primary Examiner* — Robert M Kelly
(74) *Attorney, Agent, or Firm* — WPAT, P.C.; Anthony King

(57) ABSTRACT

The present invention cloned melanin biosynthesis genes encoding polyketide synthase (PKS), scytalone dehydratase (SCD) and 1.3.8-trihydroxynaphthalene reductase (THN) from the dematiaceous *Alternasia alternate* into plasmid pCAMBIA1300, followed by transformation of the plasmid into *Matarhizium anisopliae* via *Agrobacterium tumefaciens*-mediated transformation. The transformant was able to express the abovementioned genes and synthesize melanin, which then showed enhanced UV tolerance. The transcription and expression of these melanin genes were confirmed in several pathways. The tolerances toward UV radiation, drought and high temperature were increased significantly in these transformants. In addition, the host insects were more susceptible to these transformants under UV radiation.

1 Claim, 19 Drawing Sheets

SEQUENCE LISTING

```
<160> NUMBER OF SEQ ID NOS: 37

<210> SEQ ID NO 1
<211> LENGTH: 21
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(21)
<223> OTHER INFORMATION: n is a, c, g, or t; degenerate primer for PKS
      gene of Alternaria alternate.

<400> SEQUENCE: 1
gayccnmgnt tyttyaayat g                                              21

<210> SEQ ID NO 2
<211> LENGTH: 20
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(20)
<223> OTHER INFORMATION: n is a, c, g, or t; degenerate primer for PKS
      gene of Alternaria alternata.

<400> SEQUENCE: 2
gtnccngtnc crtgcatytc                                                20

<210> SEQ ID NO 3
<211> LENGTH: 18
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(18)
<223> OTHER INFORMATION: degenerate primer for SCD gene of Alternaria
      alternata

<400> SEQUENCE: 3
tccaaggact gggaccgt                                                  18

<210> SEQ ID NO 4
<211> LENGTH: 17
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(17)
<223> OTHER INFORMATION: degenerate primer for SCD gene of Alternaria
      alternata
```

-continued

```
<210> SEQ ID NO 5
<211> LENGTH: 18
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(18)
<223> OTHER INFORMATION: degenerate primer for THN gene of Alternaria
      alternata

<400> SEQUENCE: 5
gcaaggtcgc cgttgtta                                                  18

<210> SEQ ID NO 6
<211> LENGTH: 18
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(18)
<223> OTHER INFORMATION: degenerate primer for THN gene of Alternaria
      alternata

<400> SEQUENCE: 6
cagtcaccgt cttgagaa                                                  18

<210> SEQ ID NO 7
<211> LENGTH: 22
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(22)
<223> OTHER INFORMATION: primer for sequencing in shotgun library
      construction

<400> SEQUENCE: 7
tgcaaggcga ttaagttggg ta                                             22

<210> SEQ ID NO 8
<211> LENGTH: 23
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(23)
<223> OTHER INFORMATION: primer for sequencing in shotgun library
      construction

<400> SEQUENCE: 8
cttccggctc gtatgttgtg tgg                                            23

<210> SEQ ID NO 9
<211> LENGTH: 25
<212> TYPE: DNA
<213> ORGANISM: Artificial Sequence
<220> FEATURE:
<223> OTHER INFORMATION: artificial sequence designed as a primer
<220> FEATURE:
```

<400> SEQUENCE: 4
gtgggcgtgg cccttga                                                   17

```
<221> NAME/KEY: misc_feature
<222> LOCATION: (1)..(25)
<223> OTHER INFORMATION: primer for RACE (SCD gene)

<400> SEQUENCE: 9
gcgacctttg tgcgtgtctc atccg                                          25

<210> SEQ ID NO 10
<211> LENGTH: 27
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(27)
<223> OTHER INFORMATION: primer for RACE (SCD gene)

<400> SEQUENCE: 10
ccacctgagg attgactccg ctcgttc                                        27

<210> SEQ ID NO 11
<211> LENGTH: 27
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(27)
<223> OTHER INFORMATION: primer for RACE (THN gene)

<400> SEQUENCE: 11
tacgccgcct tagcgacgaa gaactga                                        27

<210> SEQ ID NO 12
<211> LENGTH: 27
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(27)
<223> OTHER INFORMATION: primer for RACE (THN gene)

<400> SEQUENCE: 12
catcaacacc cgtggtcagt tcttcgt                                        27

<210> SEQ ID NO 13
<211> LENGTH: 19
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(19)
<223> OTHER INFORMATION: primer for primer walking (SCD gene)

<400> SEQUENCE: 13
gctacgaatg ggcagacag                                                 19

<210> SEQ ID NO 14
<211> LENGTH: 17
<212> TYPE: DNA
<213> ORGANISM: Artificial Sequence
<220> FEATURE:
<223> OTHER INFORMATION: artificial sequence designed as a primer
<220> FEATURE:
```

```
<221> NAME/KEY: misc_feature
<222> LOCATION: (1)..(17)
<223> OTHER INFORMATION: primer for primer walking (SCD gene)

<400> SEQUENCE: 14
cctcggcgaa gaccttg                                                     17

<210> SEQ ID NO 15
<211> LENGTH: 40
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(40)
<223> OTHER INFORMATION: primer for design of AvrII restriction site

<400> SEQUENCE: 15
tcacatccat cctcctgcag gatcctttgc cctagacggc                            40

<210> SEQ ID NO 16
<211> LENGTH: 40
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(40)
<223> OTHER INFORMATION: primer for full-length genomic DNA cloning of
      PKS gene

<400> SEQUENCE: 16
ggagggcggc atattcgcct aggctgtgac caatgacagc                            40

<210> SEQ ID NO 17
<211> LENGTH: 40
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(40)
<223> OTHER INFORMATION: primer for full-length genomic DNA cloning of
      PKS gene

<400> SEQUENCE: 17
tgacaccttc gggcgcgcca gagtatatgt atgctgaaga                            40

<210> SEQ ID NO 18
<211> LENGTH: 40
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(40)
<223> OTHER INFORMATION: primer for full-length genomic DNA cloning of
      PKS gene

<400> SEQUENCE: 18
gctgtcattg gtcacagcct aggcgaatat gccgccctcc                            40

<210> SEQ ID NO 19
<211> LENGTH: 39
<212> TYPE: DNA
<213> ORGANISM: Artificial Sequence
```

```
<220> FEATURE:
<223> OTHER INFORMATION: artificial sequence designed as a primer
<220> FEATURE:
<221> NAME/KEY: misc_feature
<222> LOCATION: (1)..(39)
<223> OTHER INFORMATION: primer for construction of contained binary
      vector (THN gene)

<400> SEQUENCE: 19
atgaccagca tgttggctcc gccgcctcca ccatttgta                              39

<210> SEQ ID NO 20
<211> LENGTH: 38
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(38)
<223> OTHER INFORMATION: primer for construction of contained binary
      vector (THN gene)

<400> SEQUENCE: 20
ataggcctcg agtctattcc tttgccctca gacgagtg                               38

<210> SEQ ID NO 21
<211> LENGTH: 34
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(34)
<223> OTHER INFORMATION: primer for construction of right side of binary
      vector

<400> SEQUENCE: 21
ttgagggtac catccgccgc ctccaccatt tgta                                   34

<210> SEQ ID NO 22
<211> LENGTH: 32
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(32)
<223> OTHER INFORMATION: primer for construction of right side of binary
      vector

<400> SEQUENCE: 22
ggcgcgccgt acttcctgca gggaaataaa gg                                     32

<210> SEQ ID NO 23
<211> LENGTH: 43
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(43)
<223> OTHER INFORMATION: primer for construction of right side of binary
      vector

<400> SEQUENCE: 23
cctgcaggca gtacggcgcg ccggaaccac ttaacgttac tga                         43
```

```
<210> SEQ ID NO 24
<211> LENGTH: 35
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(35)
<223> OTHER INFORMATION: primer for construction of right side of binary
      vector

<400> SEQUENCE: 24
ttgcatgcct aagcttcgag tggagatgtg gagtg                                35

<210> SEQ ID NO 25
<211> LENGTH: 37
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(37)
<223> OTHER INFORMATION: primer for construction of right side of binary
      vector

<400> SEQUENCE: 25
ctgaaggcct gcaggtcatc acaaccactc tcatcac                              37

<210> SEQ ID NO 26
<211> LENGTH: 35
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(35)
<223> OTHER INFORMATION: primer for construction of right side of binary
      vector

<400> SEQUENCE: 26
ttattggcgc gccgtgctta aacgtttcat tatct                                35

<210> SEQ ID NO 27
<211> LENGTH: 37
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(37)
<223> OTHER INFORMATION: primer for construction of left side of binary
      vector (SCD gene)

<400> SEQUENCE: 27
acatcaccat ggtgagcaag ggcgaggagc tgttcac                              37

<210> SEQ ID NO 28
<211> LENGTH: 37
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(37)
<223> OTHER INFORMATION: primer for construction of left side of binary
      vector (SCD gene)
```

<400> SEQUENCE: 28
ataggcctcg agtctatttg tacagctcgt ccatgcc                                    37

<210> SEQ ID NO 29
<211> LENGTH: 39
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(39)
<223> OTHER INFORMATION: primer for construction of left side of binary
      vector (SCD gene)

<400> SEQUENCE: 29
cttgctcacc atggtgatgt ctgctcaagc ggggtagct                                  39

<210> SEQ ID NO 30
<211> LENGTH: 36
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(36)
<223> OTHER INFORMATION: primer for construction of right side of binary
      vector (SCD gene)

<400> SEQUENCE: 30
ctgaaggcct gcaggcagtt taaacatctc ccacga                                     36

<210> SEQ ID NO 31
<211> LENGTH: 36
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(36)
<223> OTHER INFORMATION: primer for construction of right side of binary
      vector (SCD gene)

<400> SEQUENCE: 31
ttattggcgc gccggtcaag cctatcattg ttcgta                                     36

<210> SEQ ID NO 32
<211> LENGTH: 18
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(18)
<223> OTHER INFORMATION: primer for preparing probe of PKS gene

<400> SEQUENCE: 32
tgggtgttga tgtttccg                                                         18

<210> SEQ ID NO 33
<211> LENGTH: 18
<212> TYPE: DNA
<213> ORGANISM: Artificial Sequence
<220> FEATURE:
<223> OTHER INFORMATION: artificial sequence designed as a primer
<220> FEATURE:

-continued

```
<221> NAME/KEY: misc_feature
<222> LOCATION: (1)..(18)
<223> OTHER INFORMATION: primer for preparing probe of PKS gene

<400> SEQUENCE: 33
atcttggggt ccattggc                                              18

<210> SEQ ID NO 34
<211> LENGTH: 24
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(24)
<223> OTHER INFORMATION: primer for RT-PCR

<400> SEQUENCE: 34
aggtcatcca cgacaagttc acca                                       24

<210> SEQ ID NO 35
<211> LENGTH: 24
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(24)
<223> OTHER INFORMATION: primer for RT-PCR

<400> SEQUENCE: 35
accaggagac cagcttgaca aagt                                       24

<210> SEQ ID NO 36
<211> LENGTH: 20
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(20)
<223> OTHER INFORMATION: primer for RT-PCR

<400> SEQUENCE: 36
gccgtatcgt cttccgcaat                                            20

<210> SEQ ID NO 37
<211> LENGTH: 20
<212> TYPE: DNA
<213> ORGANISM: Artificial Sequence
<220> FEATURE:
<223> OTHER INFORMATION: artificial sequence designed as a primer
<220> FEATURE:
<221> NAME/KEY: misc_feature
<222> LOCATION: (1)..(20)
<223> OTHER INFORMATION: primer for RT-PCR

<400> SEQUENCE: 37
ccttcttggc tccacccttc                                            20
```

FUNGI TRANSFORMANT FOR MELANIN PRODUCTION AND USES THEREOF

BACKGROUND OF THE INVENTION

1. Field of the Invention

Figure 1:
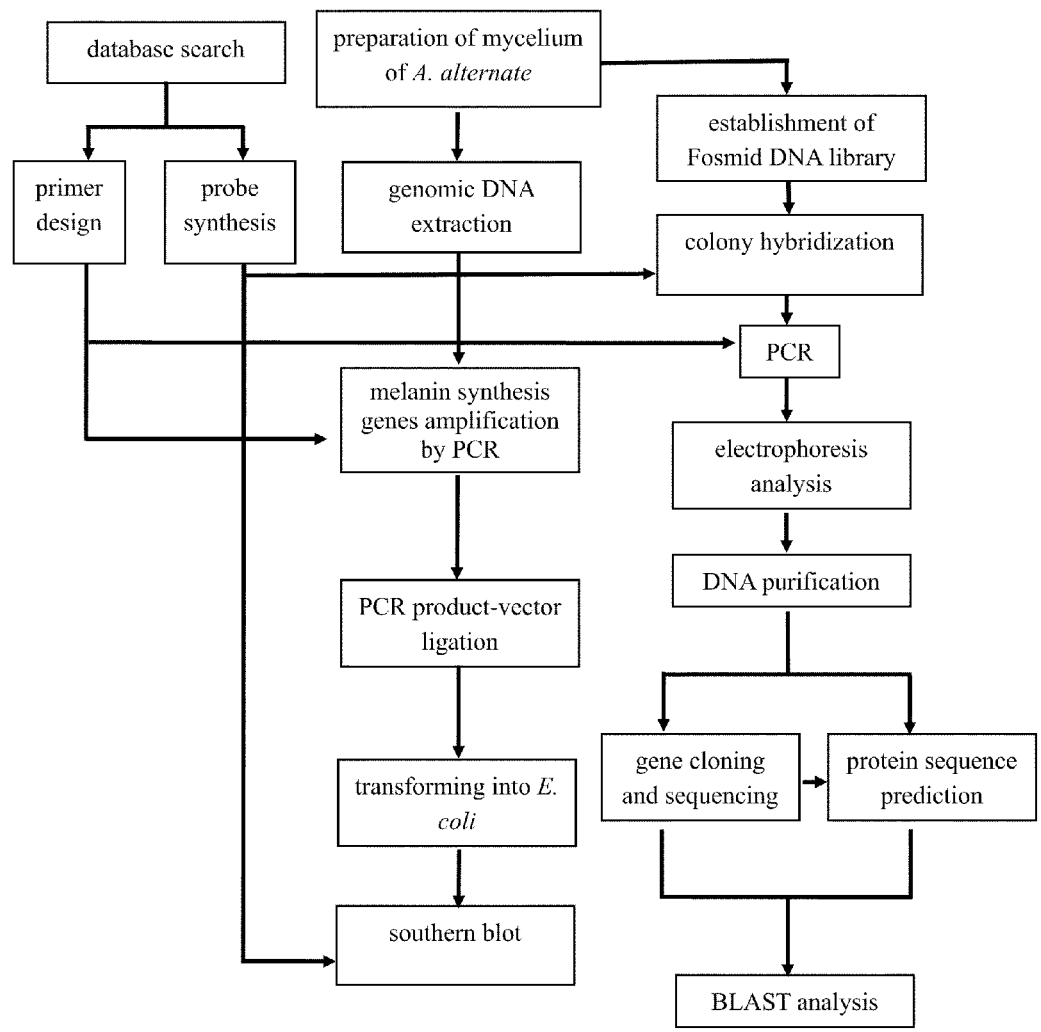

The present invention relates to a microorganism biocontrol agent, in particular to a fungi transformant containing melanin biosynthesis genes to increase the tolerance to environmental stress and its method.

2. The Prior Arts

Beneficial microorganisms such as *Metarhizium* spp., *Beauveria* spp., *Trichoderma* spp. and *Bacillus* spp. have been applied in pest management for a long time. There are numerous studies showing positive effects in pest control with beneficial microorganisms in field application so far (Genthner et al., 1998). However, the stability and reproducibility of the studies were limited in field application due to the factors of stressful environmental condition. (Alves et al., 1998; Hedgecock et al., 1995). Natural environmental factors such as high temperature, drought and UV radiation are the bottle necks for field application (Fargues, 1996). Therefore, it becomes an important issue to protect the beneficial microorganisms to lower the stress of the environment.

The survival of biocontrol microorganisms in field during the contact and application period for the strain of biological control microorganism and the targets (such as pest or pathogens) is important for tolerance of stressful environment. The application effects won't be stable for those that can not overcome the barriers and survive in field. Therefore, the improvement of tolerance to stressful environment for the biocontrol microorganism is an important issue. At present, the improvement is employed through formulation. Hedimbi et al (2008) used olive oil containing commercial sunscreens as additive to treat *Metarhizium anisopliae* conidia, and exposed them to an artificial UV source for up to 5 hours. Survival of conidia in oil formulation was around 29-40% while in control (water) was 4%. The conidial germination rates produced from mycelium were lowered to 20% when irradiated with UV-A for 6 hours (Rangel et al. 2008). The increased osmotic stress also made the germination rate of *M. anisopliae* dropped sharply. *Bacillus thuringiensis* is a biocontrol agent other than eukaryotes. The δ-endotoxin produced in *B. thuringiensis* is easily degraded by UV-radiation. The activity of *B. thuringiensis* is lost under short term exposure of sunshine. Previous studies have shown that the UV tolerance was increased in melanin producing *B. thuringiensis* strains. To overcome the stressful conditions mentioned above, the adjustment on application time (to avoid the strong light), formulation change (such as using oil to overcome the drought problem) or adding sunscreen to protect the microorganisms were employed. In addition, nutritional stress has been applied to increase the tolerance to high temperature, low water content and UV radiation. Trehalose and mannitol levels were accumulated in *M. anisopliae* conidia after nutritional stress, which may be the reason for high tolerance to the stressful condition (Rangel et al., 2008).

Biosynthesis of DHN melanin is synthesized by a polyketide pathway, through the genes encoding Polyketide synthase (PKS), Scytalone dehydratase (SCD), and 1,3,8-trihydroxynaphthalene reductase (THN). It started with a PKS using malonyl-CoA as a substrate to produce 1,3,6,8-tetrahydroxynaphthalene, 1,3,6,8-THN (Fujii et al., 2000), followed by reducatse catalysis to produce scytalone, dehydration by SCD to yield 1,3,8-trihydroxynaphthalene (1,3,8-THN), reduction by THN to yield vermelone, dehydration to produce melanin precursor 1,8-dihydroxynaphthalene (1,8-DHN), and then oxidation and polymerization to yield melanin.

Melanin is polymer existed broadly in organisms in nature and has a variety of biological functions (Hill et al., 1992). It is negatively charged, hydrophobic pigment with high molecular weight, which is formed by the oxidative polymerization of phenolic and/or indolic compounds. In many organisms, melanin protects cells from stressful conditions, such as oxidation, extreme temperature, UV radiation, chemical, and biochemical stresses (reviewed in Nosanchuk and Casadevall, 2003; Bell and Wheeler, 1986). Therefore, the use of melanin in the invention is a solution to protect biocontrol agents.

SUMMARY OF THE INVENTION

Microorganisms such as *M. anisopliae* used as the biocontrol agents need to tolerate the environmental stresses during the period to interact with target organisms (pests or pathogens). The survival of the biocontrol agent is quite important in the field. The activity would be unstable if the abovementioned barriers were not overcome. It remains to be an important issue to improve the stress tolerance of the biocontrol agents.

The objective of the present invention is to provide a vector expressing melanin biosynthesis proteins, a transforming mediator having the vector, and a fungi transformant expressing melanin biosynthesis.

The fungi transformant of the present invention is an *M. anisopliae* transformant which was deposited in the Deutsche Sammlung Von Mikroogranismen and Zellkulturen GMBH (DSMZ), located at Inhoffenstr. 7B D-38124 Braunschweig with an accession number DSM 27044, Deposited on Mar. 20, 2013. The vectors were plasmids pCAMBIA PKS-ORF, pCAMBIA scy and pCAMBIA THN which were also deposited under the accession number BCRC 940577, BCRC 940578 and BCRC 940579 respectively in the Culture Collection and Research Center (CCRC) of Taiwan with an accession number of BCRC940577 on Dec. 24, 2009.

Another objective of the present invention is to provide a method for preparing a fungi transformant expressing melanin biosynthesis, which may be made through the following example, but is not limited to the materials and steps mentioned below.

Yet another objective is to provide applications of biocontrol agents using fungi transformants.

A technique has been employed to solve the problems of the prior art, where the melanin biosynthesis genes from Alternaria alternate has been cloned and transferred into the beneficial microorganisms to protect the target microorganisms. The beneficial microorganism in the present invention is *M. anisopliae* which could parasitize in many major pests. The melanin biosynthesis genes from *Alternaria alternate* include genes encoding polyketide synthase (PKS), scytalone dehydratase (SCD), and 1,3,8-trihydroxynaphthalene reductase (THN). *M. anisopliae* is able to synthesize melanin after these three genes were cloned into the *A. tumefaciens* plasmid pCAMBIA 1300 respectively, followed by *A. tumefaciens*—mediated transformation into *M. anisopliae*. The melanin can be produced in a non-melanin producing fungi through the cloning and transformation of DHN melanin biosynthesis gene.

The transformants of *M. anisopliae* according to the present invention can effectively increase the tolerance to UV radiation, extreme temperature or low temperature, and drought. The protective method using microorganisms to synthesize melanin directly, which is different from the traditional way by adding anti-UV compounds to microorganisms, increases the survival potential, shows higher and faster infection ability in stressful environment, further increases the application efficiency of beneficial microorganisms. In the future, the present invention can be applied in other beneficial microorganisms and plants to enhance the tolerance of stressful conditions.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The related drawings in connection with the detailed description of the present invention to be made later are described briefly as follows, in which:

FIG. 1 is the flowchart for cloning of DHN melanin biosynthesis gene from *A. alternate;*

FIG. 2 shows results of PCR amplification toward complete genome using degenerate primers in electrophoresis;

FIG. 3 shows the diagram of functional motifs of PKS gene from *A. alternate* after compared with Propom search utility;

FIGS. 4A and 4B are diagrams showing the genomic DNA of SCD and THN genes respectively;

FIG. 5 is the flowchart for establishing transformant of *M. anisopliae* and the analysis of physiology and biochemistry;

FIGS. 6A and 6B are diagrams for primer designing in constructing of plasmid pGEM-GT and plasmid pGEM-GF respectively;

FIGS. 7A to 7E are the flowcharts for construction of PKS containing transformation plasmid;

FIGS. 8A to 8C are plasmid maps for PKS transformation plasmid (A), SCD transformation plasmid (B), and THN transformation plasmid (C) respectively;

FIG. 9 shows front and reverse colonial morphology of wild type and transformant *M. anisopliae;*

FIGS. 10A to 10C are Southern blot analysis on PKS, SCD and THN from *A. alternate*, wild type and transformant *M. anisopliae* respectively, where (A): SCD, (B): THN, and (C): PKS;

FIG. 11 shows the electrophoresis of RT-PCR on PKS, SCD and THN from *A. alternate*, wild type and transformant *M. anisopliae;*

FIG. 12 is the spectra analysis of DOPA-melanin and DHN-melanin from transformant *M. anisopliae* MA05-169 using Electron Paramagnetic Resonance technique;

FIG. 13 is the spectra analysis of DOPA-melanin and DHN-melanin from transformant *M. anisopliae* MA05-169 using UV-Vis spectrophotometry;

FIG. 14 shows the results after applying linear regression to log-spectra of FIG. 13;

FIG. 15 is the spectra analysis of DOPA-melanin and DHN-melanin from transformant *M. anisopliae* MA05-169 using FT/IR;

FIGS. 16A to 16F are LC/MS analysis on the melanin intermediates: (A) 1.3.6.8-THN, (B) 1.3.8-THN, (C) Scytalone, (D) Vermelone, (E) Flaviolin, and (F) 2-hydroxyjuglone;

FIGS. 17A to 17C are the virulence tests of wild type and transformant *M. anisopliae* using $3^{rd}$ instar larvae of *P. xylostella;*

FIGS. 18A to 18D are the results of conidial germination assay of wild type and transformant *M. anisopliae* undertaken in UV-B radiation stress studies.

DETAILED DESCRIPTION OF THE PREFERRED EMBODIMENT

Definition:

The term "biocontrol microorganisms or biocontrol agent" as used herein refers to microorganisms or the active components used for pest or pathogen control, which are formulated as a product and the sources of microorganism include bacteria, fungi, virus and protozoa.

The term "stressful environment" as used herein refers to unfavorable conditions such as UV-radiation, drought, extreme high or low temperature to the survival of microorganism.

The term "transformant" as used herein refers to an organism that has undergone transformation to receive foreign genes.

The term "vector" as used herein refers to a nucleic acid molecule capable of self-duplicating and receiving foreign genes by insertion, and transporting foreign genes into a receiver DNA through transformation.

Example 1

(1) Cloning of Melanin Biosynthesis Genes

Referring to FIG. 1, the flowchart for cloning of DHN melanin biosynthesis gene from *A. alternata* BCRC30501 was shown. The detailed steps for cloning of the genes encoding Polyketide synthase (PKS), Scytalone dehydratase (SCD), and 1,3,8-trihydroxynaphthalene reductase (THN) were described below.

(2) Strains and Vectors

The fungi including *A. alternata* BCRC30501 and *M. anisopliae* BCRC35505 used in the present invention were obtained from Food Industry Research and Development Institute, Taiwan. Binary vector pCMABIA 1300 (NCBI gi:7638064) (Canberra, Australia) was used as backbone for plasmid construction (Hajdukiewicz et al., 1994).

(3) Establishment of Genomic DNA Library

The mycelium of *A. alternate* was harvested after cultivation for DNA extraction (according to Al-Samarrai, 2000). The genomic DNA library of *A. alternate* was obtained with the kit of CopyControl™ Fosmid library production kit (Epicentre, Madison, Wis., USA). The clones were dotted on a nylon filter for screening. 7000 colonies were dotted in duplicate on nylon filter (22×22 cm) using a robotic arm for Southern blot analysis.

(4) Primer Pairs and DIG Probes

DHN melanin biosynthesis genes including PKS, SCD and THN genes were collected form NCBI (USA). Degenerate primers were designed after the conserved regions were analyzed. PCR reactions using primer pairs listed below and *A. alternate* genomic DNA were carried out to yield 700 bp, 250 bp, and 750 bp fragments respectively. Degenerate primers used were:

```
KS1:
5'-GAY CCN MGN TTY TTY AAY ATG-3'; (SEQ ID NO: 1)

KS2:
5'-GTN CCN GTN CCR TGC ATY TC-3';  (SEQ ID NO: 2)

scyA:
5'-TCC AAG GAC TGG GAC CGT-3';     (SEQ ID NO: 3)

scyB:
5'-GTG GGC GTG GCC CTT GA-3';      (SEQ ID NO: 4)

1,3,8-tri(A):
5'-GCA AGG TCG CCG TTG TTA-3';     (SEQ ID NO: 5)
```

-continued 1,3,8-tri(B):
5'-CAG TCA CCG TCT TGA GAA G-3'.    (SEQ ID NO: 6)

Figure 2:
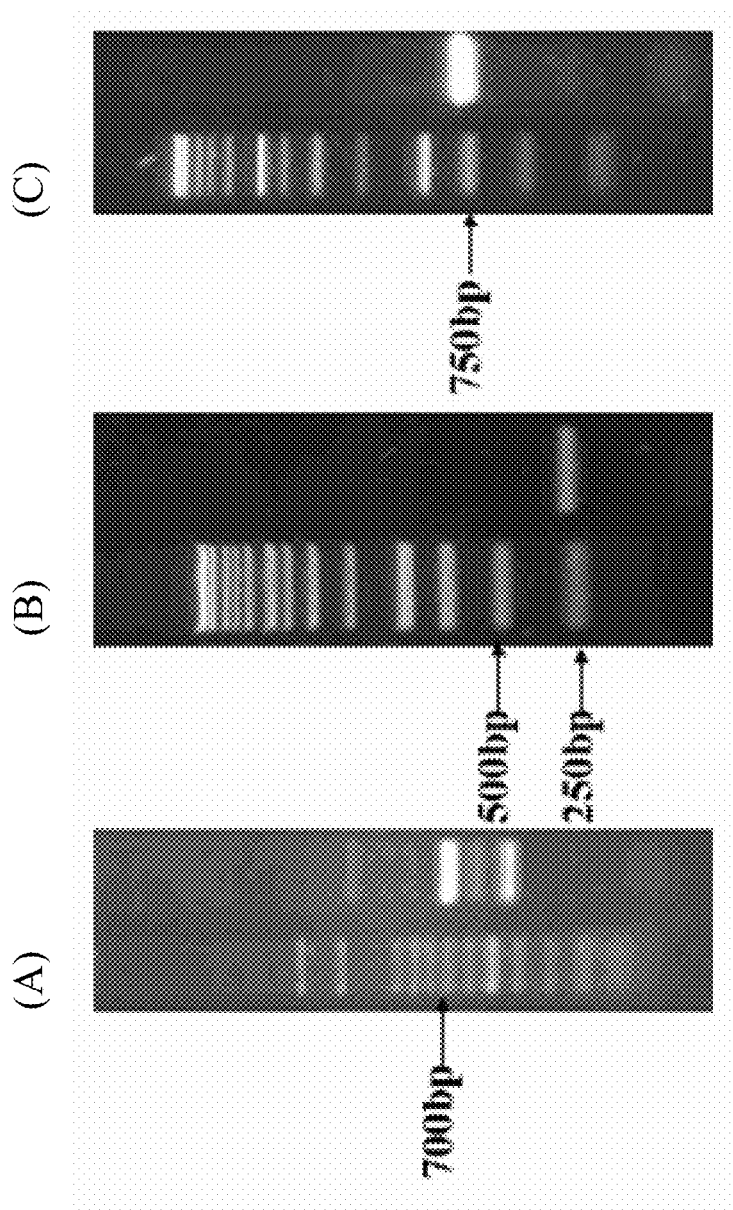

The results of PCR amplification in electrophoresis are shown in FIG. 2. FIG. 2A displayed a 700 bp fragment after PCR using primer pair of KS1 and KS2. FIG. 2B displayed a 250 bp fragment after PCR using primer pair of scyA and scyB. FIG. 2C displayed a 750 bp fragment after PCR using primer pair of 1,3,8-tri(A) and 1,3,8-tri(B).

The PCR products were cloned into pGEM®-T (Promega, Wis., USA) and analyzed the sequences. The melanin biosynthesis gene sequences were confirmed with the NCBI GenBank with BLAST. DIG labeling probe was produced with the abovementioned primer pairs and PCR DIG probe synthesis kit (Roche, USA). The following ingredients were added respectively and mixed thoroughly before PCR amplification. The plasmids in the reaction were obtained from PCR product and pGEM-T cloning.

| | |
|---|---|
| ddH₂O | 32.25 µl |
| 10X PCR buffer | 5 µl |
| DIG mix | 5 µl |
| 20 µM primer A | 1 µl |
| 20 µM primer B | 1 µl |
| plasmid DNA (20 ng/µl) | 5 µl |
| enzyme | 0.75 µl |

(5) Gene Cloning and Nucleotide Sequence Analysis

The DIG probes were used as probes for Southern Blot analysis with the Fosmid library of *A. alternate*. The clone aaf01018E was found to contain PKS and THN encoding genes, which was used in Shotgun library construction. The Fosmid clone was analyzed for the complete sequence.

(6) Shotgun Library Construction

The genomic DNA of clone aaf01018E was sheared into small fragments with Hydroshear (Gene Machine), and the ends were trimmed with Bal 31 nuclease and T4 DNA polymerase. The 2 kb-3 kb fragments of the abovementioned DNAs were separated after electrophoresis and recovered with QIAquick Gel Extraction kit (Qiagen). The recovered DNAs were subcloned into pUC18 vector and transformed into *E. coli* DH5α (Life Technologies) competent cells through heat shock with ampicillin selection and X-gal screening. The DNA of the transformant was purified and sequence analyzed by Big dye terminator ver 3.1 (Applied Biosystems) using ABI 3730x1 DNA analyzer. The sequencing primers used were:

M13FW:
5'-TGCAAGGCGATTAAGTTGGGTA-3'    (SEQ ID NO: 7)

M13REW2:
5'- CTTCCGGCTCGTATGTTGTGTGG-3'.    (SEQ ID NO: 8)

The sequences obtained were assembled with a Phred/Phrap/Consed software developed in University of Washington (Phrap version 0.990329, and Consed version 13) to yield a 40 kb sequence.

(7) Reverse Transcription PCR(RT-PCR)

Total RNA of *A. alternate* was extracted and treated with DNase. To one µl of the treated RNA, 0.3 µl of 10 µM of dT18 mer, 1.0 µl of 10 mM dNTP and 10.7 of DEPC treated ddH₂O were added and mixed at 65° C. for 5 min. Then 4 µl of 5× First-strand buffer, 1 µl of 0.1 M DTT (1,4-dithiothreitol), 1 µl of RNase out and of SuperScript III reverse transcriptase (Invitrogen) were added and mixed at 50° C. for 35 min followed by 70° C. for 15 min to stop the reverse transcriptase reaction. PCR amplification was carried out with this cDNA as template using ScyA, ScyB and 1,3,8-tri(A), 1,3,8-tri(B) primer pair to generate cDNA fragments of scytalone dehydratase (SCD) and 1,3,8-trihydroxynaphthalene reductase (THN). These cDNA fragments can be used for primer design in rapid amplification of cDNA (RACE) after these sequences were determined.

(8) Rapid Amplification of cDNA Ends (RACE)

The RACE of SCD and THN genes were carried out with GeneRacer™ kit (Invitrogen, USA) according to the manual.

The cDNA obtained from GeneRacer™ kit was used again for RACE. The primers were designed after the abovementioned SCD and THN gene sequences were determined:

SCD:
5'-anti
GCGACCTTTGTGCGTGTCTCATCCG;    (SEQ ID NO: 9)

3'-sense
CCACCTGAGGATTGACTCCGCTCGTTC;    (SEQ ID NO: 10)

THN:
5'-anti
TACGCCGCCTTAGCGACGAAGAACTGA;    (SEQ ID NO: 11)

3'-sense
CATCAACACCCGTGGTCAGTTCTTCGT.    (SEQ ID NO: 12)

The PCR products after RACE were cloned into pGEM-T for construction of binary vectors.

The condition of Touch down PCR is listed in Table 1.

TABLE 1

| temperature | time | cycles |
|---|---|---|
| 94° C. | 2 min | 1 |
| 94° C. | 30 sec | 5 |
| 72° C. | 1 min/per kb | |
| 94° C. | 30 sec | 5 |
| 70° C. | 1 min/per kb | |
| 94° C. | 30 sec | 25 |
| 68° C. | 30 sec | |
| 72° C. | 1 min/per kb | |
| 72° C. | 10 min | 1 |

(9) Full Length DNA Sequence of SCD

Genes encoding PKS and THN were obtained during Fosmid cloning. The full length of SCD gene was not cloned from Fosmid clone screening. Therefore the cDNA of SCD obtained from RACE was used for primer pair designation, probe preparation and Southern blot analysis. The DNAs of clones containing SCD gene were purified and sequence determined with primer walking method to determine the full length SCD genomic DNA sequence. The primer set used were Scy_N_2-1: 5' gCTACgAATgggCAgACAg 3' (SEQ ID NO: 13) and Scy_N_2-2: 5' CCTCggCgAAgACCTTg 3' (SEQ ID NO: 14).

Figure 4A:
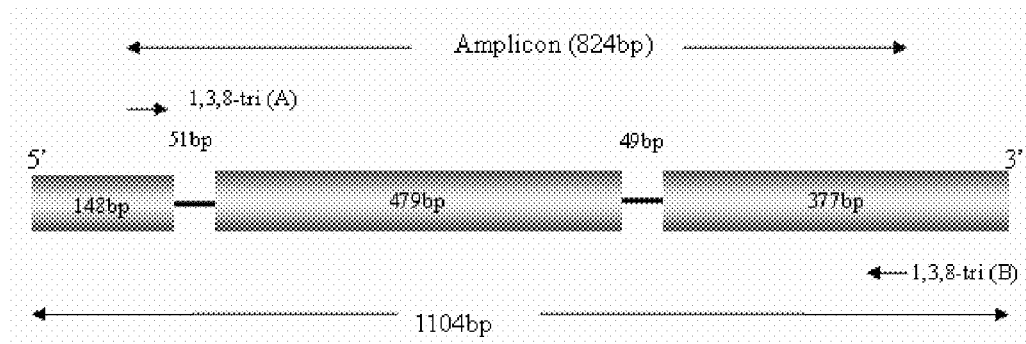
Figure 4B:
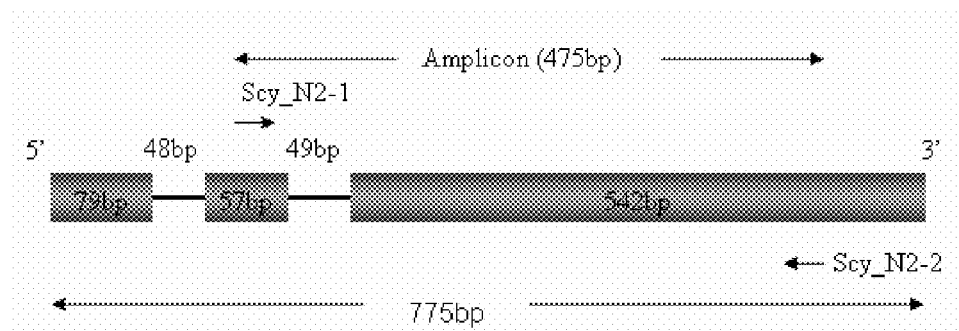

The full length gene sequences of SCD and THN were determined after cDNA cloning and genome sequence analysis (FIGS. 4A and 4B). The SCD gene has 775 bases with 2 introns of 48 bases and 49 bases respectively; while the THN gene has 824 bases with 2 introns of 51 bases and 49 bases respectively.

Figure 3:
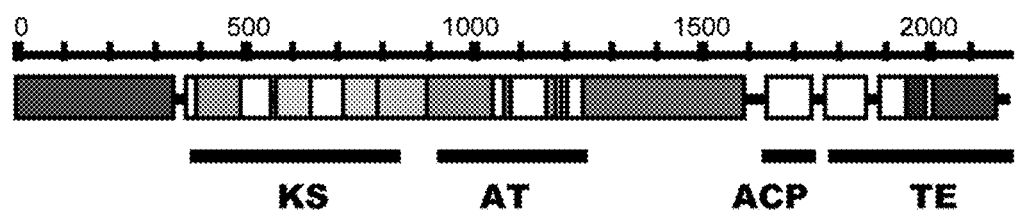

(10) Full Length DNA Sequence of PKS cDNA clone of PKS was not obtained from previous experiment. Therefore we used the genomic DNA for PKS cloning. The PKS containing Fosmid yield DNA of 40 kb in length. This sequence was compared to the GenBank data base using Basic Local Alignment Search Tool (BLAST) to determine the range of the full length PKS. The region was then compared with Propom search utility to define the functional motifs (FIG. 3) and redefine the range. The functional motifs were shown in FIG. 3 (KS: β-keto synthase motif; AT: acyl transferase motif; ACP: acyl carrier protein motif and TE: thioesterase).

Restriction enzyme AvrII showed a single site in the PKS gene range after analysis. The primer pair was designed according to this single site. PCR amplification was performed with the template of PKS containing Fosmid, and a primer pair to yield a 3-kb fragment which was designated PKS-Sbf. The primer set used were:

```
SbfI-AvrII:                        (SEQ ID NO: 15)
TCACATCCATCCTCCTGCAGGATCCTTTGCCCTAGACGGC

AvrII-SbfI:                        (SEQ ID NO: 16)
GGAGGGCGGCATATTCGCCTAGGCTGTGACCAATGACAGC.
```

PCR amplification was performed with the template of PKS containing Fosmid, and primer pair AscI-AvrII (SEQ ID NO: 17): TGACACCTTCGGGCGC GCCAGAGTATATG-TATGCTGAAGA and AvrII-AscI (SEQ ID NO: 18): GCTGT CATTGGTCACAGCCTAGGCGAAT ATGCCGC-CCTCC) to yield a 3.5-kb fragment which was designated PKS-Asc.

From the example of the present invention, the gene fragment of SCD obtained was 775 bases with 2 introns of 48 bases and 49 bases respectively; and the gene fragment of THN gene was 1104 bases with 2 introns of 51 bases and 49 bases respectively. The PKS gene fragments include PKS-Asc (3.5 kb) and PKS-Sbf (3 kb)

Example 2

(1) Construction of Transformation Vectors

Figure 5:
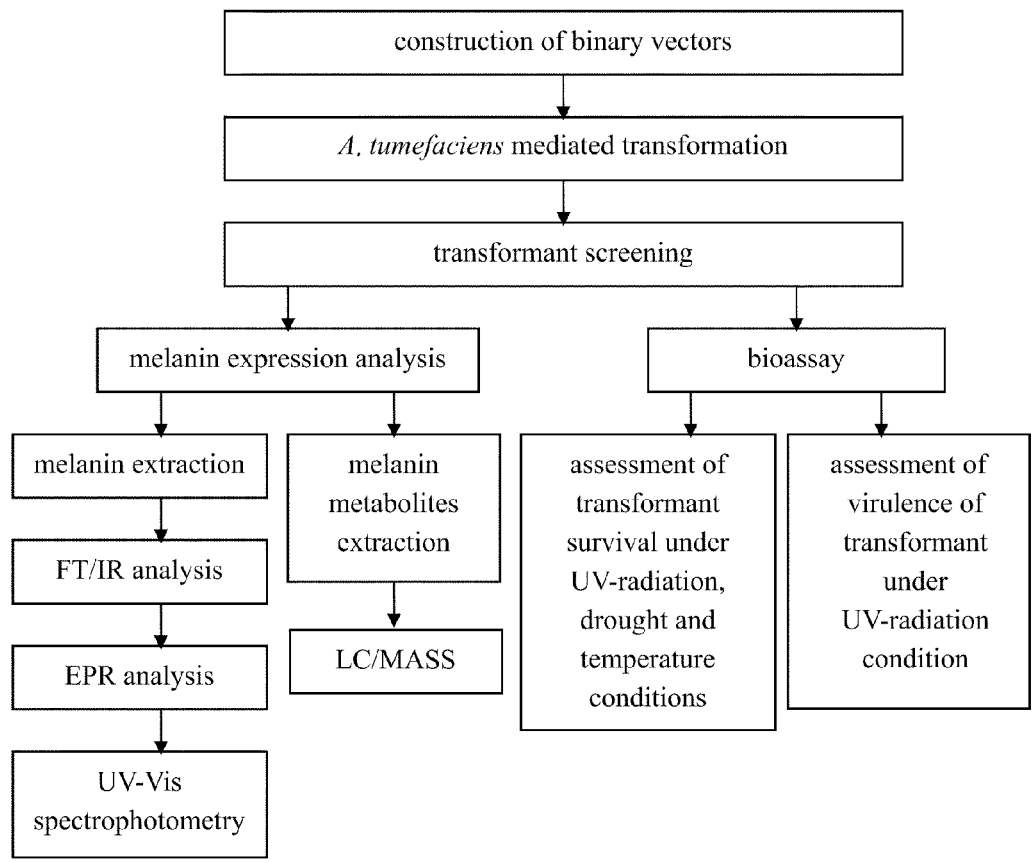

Referring to FIG. 5, the flowchart for establishing transformant of *M. anisopliae* and the analysis of physiology and biochemistry. First, the binary vector was constructed according to the present invention. Then these 3 genes were inserted into binary vector pCAMBIA 1300 respectively for *Agrobacterium*-mediated transformation.

(1) Construction of THN Gene Harboring Binary Vector

Plasmid pCAMBIA was used as binary vector backbone for transformation. The selection marker is Hygromycin$^R$ and reporter gene is green fluorescent protein (GFP), under the control of glyceraldehyde-3-phosphate dehydrogenase (GPD) promoter from *Aspergillus nidulans*. PCR amplification was performed with the template of pAN7-1 (NCBI gi: 475166), primer set of BstXI-GPD-s and Hyg-XhoI-a to clone the GPD promoter and HygromycinR gene. The primer set was designed to have a BstXI site in GDP promoter region and an XhoI site in Hygromycinr gene. The PCR product generated is 1.9 kb long and subcloned into pGEM-T easy to yield pGEM-GH.

```
BstXI-GPD-s (SEQ ID NO: 19):
5'-ATGACCAGCATGTTGGCTCCGCCGCCTCCACCATTTGTA-3'

Hyg-XhoI-a (SEQ ID NO: 20):
5'-ATAGGCCTCGAGTCTATTCCTTTGCCCTCAGACGAGTG-3'
```

(a) Construction of Left Border of the Binary Vector

The 35S promoter and CDS3 (Hygromycin resistant gene) were removed by BstXI and XhoI restriction enzyme digestion from plasmids pCAMBIA1300 and pGEM-GH, followed by ligation of 1.9 kb of GPD-Hygromycin$^R$ from pAN7-1 and resulted in pCAM-GH as the left border of the binary vector.

(b) Construction of Right Border of the Binary Vector

Two primer set was designed to contain a GDP promoter and a TrpC terminator, restriction sites in the middle and both ends. PCR amplification was performed with the template of pAN7-1 (NCBI gi: 475166), and the above-mentioned primer sets to ligate these 2 fragments. The sequences of the primers were:

```
GPD-K-s:                           (SEQ ID NO: 21)
5'-TTGAGGGTACCATCCGCCGCCTCCACCATTTGTA-3',

GPD-S-A-a:                         (SEQ ID NO: 22)
5'-GGCGCGCCGTACTTCCTGCAGGGAAATAAAGG-3'

Trp-S-A-s:                         (SEQ ID NO: 23)
5'-CCTGCAGGCAGTACGGCGCGCCGGAACCACTTAACGTTACTGA-3',

Trp-H-a:                           (SEQ ID NO: 24)
5'-TTGCATGCCTAAGCTTCGAGTGGAGATGTGGAGTG-3'.
```

Figure 6A:
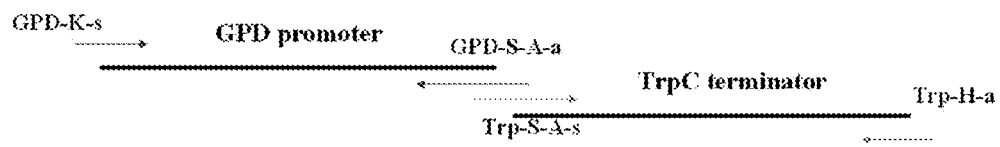

Primer set of GPD-K-s and GPD-S-A-a were used to amplify amplicon of GPD promoter; while primer set of Trp-S-A-s and Trp-H-a were used to amplify the TrpC terminator. Both PCR products were mixed as primers for each other, followed by addition of dNTP, PCR buffer and Taq DNA polymerase for 5 cycles. Final amplification was carried with primers GPD-K-s and Trp-H-a (refers to FIG. 6A). The PCR product was cloned into pGEM-T easy to yield pGEM-GT.

The plasmids pGEM-GT and pCAM-GH were digested with KpnI and HindIII. Then the fragment containing GDP promoter and TrpC terminator was ligated to pCAM-GH to yield pCAM-GH-GT.

Primer set was designed to have a full length of THN cDNA and restriction sites of SbfI and AscI. The sequence of primers are: Tri-S-s (SEQ ID NO: 25): 5'-CTGAAGGCCTGCAGGT-CATCACAACCACTCTCATCAC-3' and Tri-A-a (SEQ ID NO: 26): 5'-TTATTGGCGCGCCGTGCT-TAAACGTTTCATTATCT-3'. The PCR product was cloned into pGEM-T easy to yield GEM-TriFL.

Figure 8A:
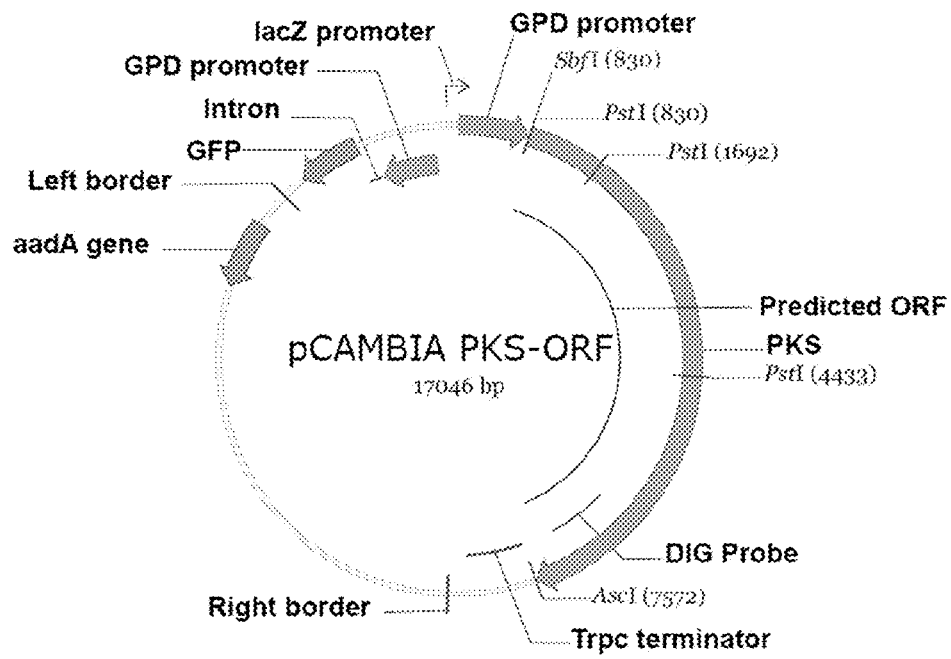
Figure 8B:
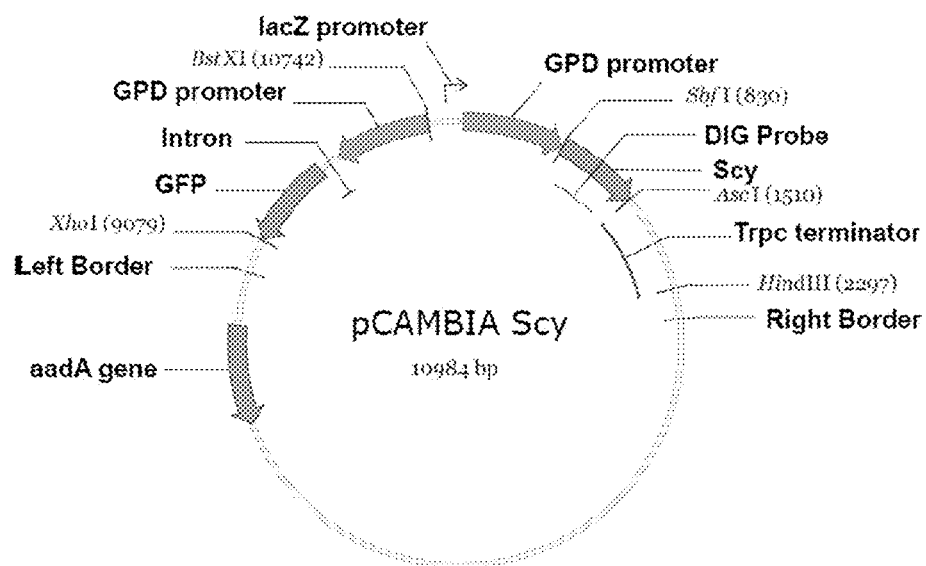
Figure 8C:
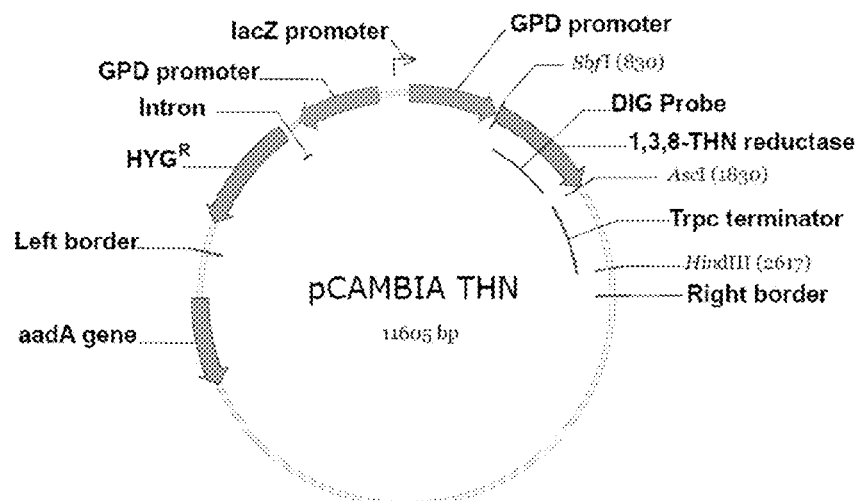

Plasmids pGEM-TriFL and pCAM-GH-GT were digested with SbfI and AscI. The full length cDNA of THN was ligated into pCAM-GH-GT to yield pCAM-GH-GT-Tri. This complete binary vector, which contains THN gene and can be used for transformation (FIG. 8C), was deposited in Culture Collection and Research Center (CCRC) of Taiwan with an accession number BCRC 940579.

(2) Construction of SCD Gene Harboring Binary Vector (a) Construction of Left Border of the Binary Vector The GPF (green fluorescent protein) gene were PCR amplified with pRF280 (Toews et al., 2004) as template to yield a 700 bp fragment. Part of the 3'-end sequence of GDP was added into the 5'-end of the sense primer; and an XhoI site was added in the 3'-end of the antisense primer. The sequence of primers are: GDP-GFP-s (SEQ ID NO: 27): 5'-ACAT-CACCATGGTGAGCAAGGG CGAGGAGCTGTTCAC-3' and GPD-GFP-XhoI-a (SEQ ID NO: 28): 5'-ATAGGCCTC-GAGTCTATTTGTACAGCTCGTCCATGCC-3'. The DGP promoter was amplified with the following primer set to yield a 1000 bp fragment. BstXI-GPD-s: 5'-ATGACCAGCATGT-TGGCTCCGCCGCCTCCACCATTTGTA-3' (the same as SEQ ID NO: 19) and GDP-GFP-a: 5'-CTTGCTCACCATG-GTGATG TCTGCTCAAGCGGGGTAGCT-3' (SEQ ID NO: 29).

Figure 6B:
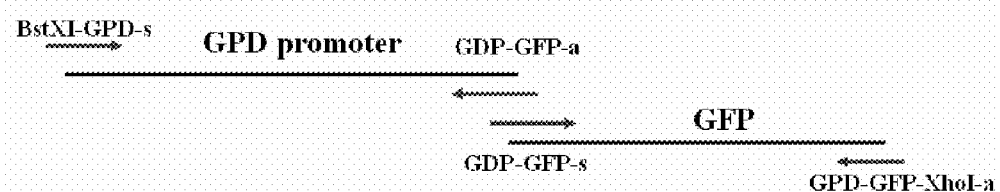
Figure 7:
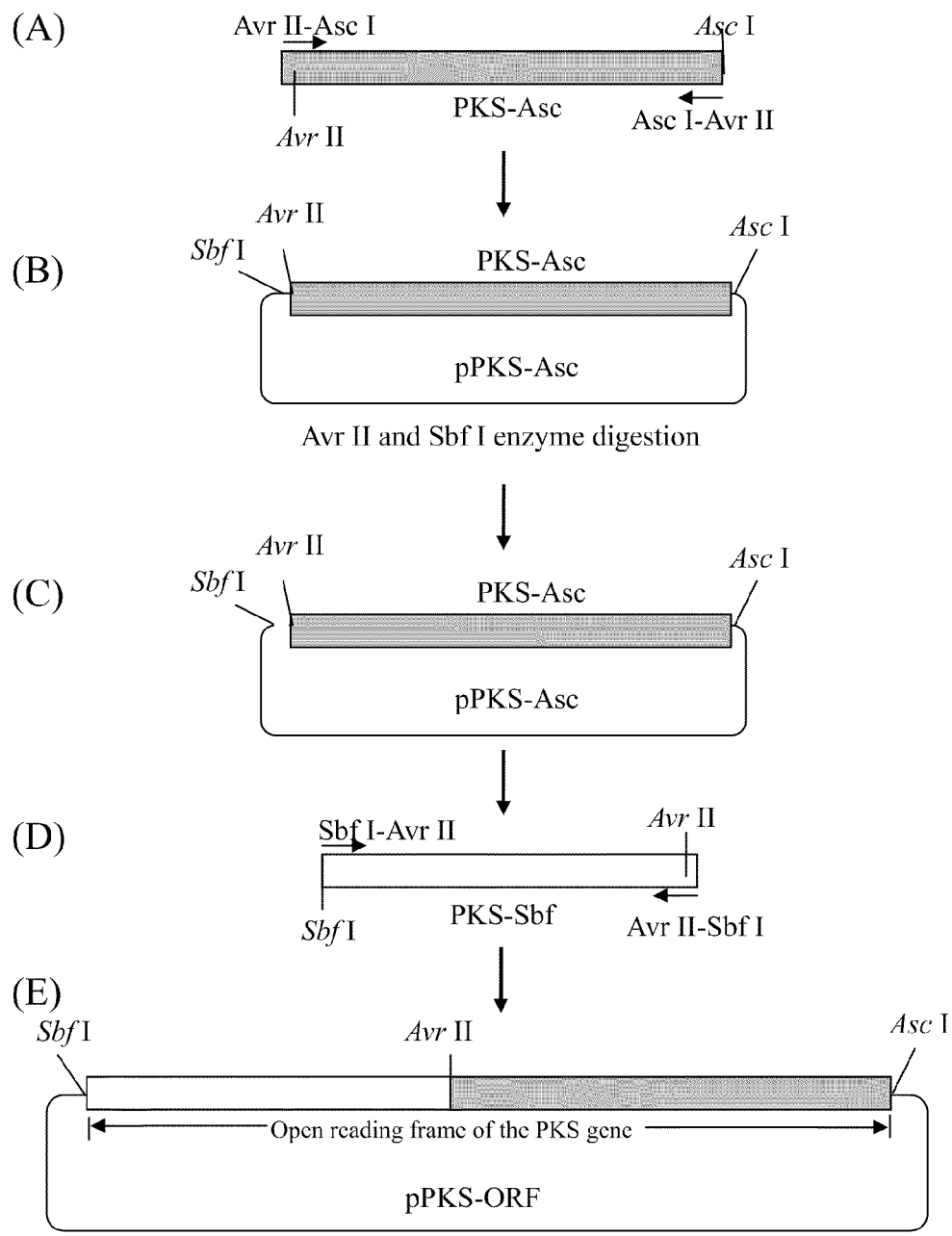

Both PCR products (700 bp for GFP and 1000 bp for GPD) were mixed as primers for each other, followed by addition of dNTP, PCR buffer and Taq DNA polymerase for 5 cycles. Final amplification was carried with primers BstXI-GPD-s and GPD-GFP-XhoI-a (refers to FIG. 6B). The 1.7 kb PCR product was cloned into pGEM-T easy to yield pGEM-GF.

Plasmids pGEM-TGF and pCAMBIA-1300 were digested with BstXI and XhoI. The fragment containing GPD promoter and GFP partial sequence was ligated with pCAMBIA to yield pCAM-GF.

(b) Construction of Right Border of the Binary Vector

Plasmids pGEM-GT and pCAM-GF were digested with KpnI and HindIII. The fragment containing GPD promoter and TrpC terminator partial sequence was ligated with pCAM-GF to yield pCAM-GF-GT. A primer set was designed to contain the full sequence of SCD cDNA and SbfI and AscI restriction site in the end. The PCR product was cloned into pGEMT-easy to yield pGEM-ScyFL. The sequences of the primer set are: Scy-S-s (SEQ ID NO: 30): 5'-CTGAAGGCCTGCAGGCAGTTTAAA-CATCTCCCACGA-3' and Scy-A-a (SEQ ID NO: 31): 5'-TTATTGGCGCGCCGGTCAAGCCTATCAT-TGTTCGTA-3'.

Plasmids pGEM-ScyFL and pCAM-GF-GT were digested with SbfI and AscI. The full length cDNA of Scy was ligated into pCAM-GF-GT to yield pCAM-GH-GT-Scy. This complete binary vector (FIG. 8B), which contains SCD gene and can be used for transformation, was deposited in Culture Collection and Research Center (CCRC) of Taiwan with an accession number BCRC 940578.

(3) Construction of Pks Gene Harboring Binary Vector

Referring to FIGS. 7A-7E, the flow chart for constructing PKS gene transforming vector. The PKS-Asc fragment was cloned into pGEM-T easy to yield pPKS-Asc. This plasmid was digested with AscI and SbfI then ligated with PKS-Sbf to yield pPKS-ORF, which contains the open reading frame (ORF) of PKS.

Plasmid pCAM-GF-GT-Scy was digested with SbfI and AscI to remove SCD cDNA. pPKS-ORF was also digested with SbfI and AscI to remove the PKS full length gDNA. The full length gDNA of PKS was ligated into pCAM-GF-GT-Scy to yield pCAM-PKS-ORF. This complete binary vector (FIG. 8A) was deposited in Culture Collection and Research Center (CCRC) of Taiwan with an accession number BCRC 940577.

Example 3

Transformation and Screening (1) Materials:
(a) Induction Medium (IM) Preparation:

A solution of 10 mM $K_2HPO_4$, 10 mM $KH_2PO_4$, 2.5 mM NaCl, 2 mM $MgSO_4$, 0.7 mM $CaCl_2$, trace amount of $FeSO_4$, 4 mM $(NH_4)2SO_4$ and 40 mM MES pH 5.3, and 0.5% glycerol was prepared and autoclaved, followed by the addition of 10 mM glucose and 200 μM acetosyringone. Acetosyringone needs to be dissolved in DMSO or 100% ETOH in the concentration of 200 mM, and then filtered with 0.45 μm filter.

(b) Co-Cultivation Medium Preparation:

The co-cultivation medium was the same as IM, except the glucose concentration of 5 mM was used, and the plate was prepared after the addition of 1.5% agar.

(2) Preparation of *Agrobacterium Tumefaciens*

*Agrobacterium tumefaciens* EHA105 containing pCAMI-BATri, pCAMBIA SCD and pCAMBIA PKS-ORF (electroporation or tri-parental mating method can be used) was cultivated in 10 ml of LB broth containing 50 μg/ml kanamycin at 28° C., 220 rpm for 18 h. The cells were washed with IM for three times after the centrifugation of 8,000 rpm for 5 min, and resuspended into IM till O.D.$_{600}$=0.30. 10 ml of the culture in IM containing 50 μg/ml kanamycin and acetosyringone was cultivated at 28°C., 220 rpm till O.D.$_{600}$=0.6-0.8.

*M. anisoplia* was cultivated in PDB at 25° C. in the dark for 2 days. The mycelia were removed with Miracloth®. The conidia were collected after centrifugation at 5,000 rpm for 5 min, aspiration of the medium and resuspension in sterile water at the concentration of $10^6$ conidia/ml.

(3) Tranformation
(a) Co-Cultivation

The conidial suspension of *M. anisopliae* was mixed with *Agrobacterium tumefaciens* containing PKS, SCD and THN respectively. And 100 l of the mixture was spread to the semi-permeable membrane covered co-cultivation solid medium for cultivation at 28° C. for 2 days. The semi-permeable membrane was cut into 1 cm width with a sterile knife and transferred into CPZ medium (Difco) containing 250 μg ml$^{-1}$ cefotaxime and hygromycein (100 μg/ml), with the conidium-containing side facing down and 1 cm apart. The colonies obtained after 7 days in the surface of the membrane were transferred again into CPZ medium (Difco) containing 250 μg ml$^{-1}$ cefotaxime and hygromycein (100 μg/ml).

(c) Screening of Transformant

The *M. anisopliae* transformant MA05-169 was deposited in Deutsche Sammlung Von Mikroorganismen and Zellkulturen GMBH (DSMZ) on Mar. 20, 2013, with an accession number of DSM 27044. The screening steps were descried below.

Figure 9:
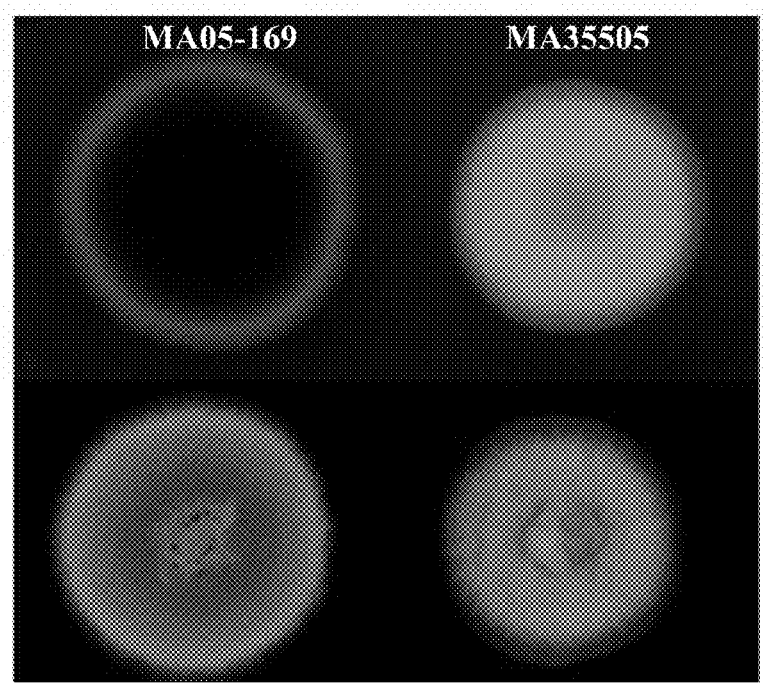

The candidate strains in CPZ medium were subcultured first, then the residual mycelia was collected in a 2 ml tube, followed by addition of steel beads and shaking at 1300 rpm to break down the cells. The genomic DNA was extracted with Maxwell® 16 genomic DNA Purification Kits (Promaga, USA). PCR amplification was performed with this genomic DNA and primers of PKS-TE-sen, PKS-TE-anti, Scy_N_2-1, Scy_N_2-2 and Tri (A), Tri (B) to confirm the melanin synthesizing gene in the candidate strains. Transformants containing melanin synthesizing gene were cultivated in PDA medium containing hygromycein (100 μml$^{-1}$). PCR amplification was carried out again after 5 times of subculture to confirm the existence of each gene. The *M. anisopliae* transformant MA05-169 was selected for the following experiment. The colony morphology of wild type *M. anisopliae* MA35505 and transformant MA05-169 were shown in FIG. 9, with the former on the left and the latter on the right.

(d) Southern Blot Hybridization

The genomic DNAs of *A. alternate, M. anisopliae* MA35505 and *M. anisopliae* MA05-169 were prepared according to Al-Samarrai et al (2000). Restriction enzyme digestion with Hind III was carried out with SCD and THN detection, and PstI was carried out with PKS detection. The digested DNA was separated by electrophoresis in a 0.8% agarose at 50 v for 6 h, and transferred to nylon membranes according to the procedures in Molecular cloning (Sambrook and Russell, 2001). Hybridization probes were synthesized with PCR amplification and labeled with DIG according to the manufacturer's instruction (Roche). The sequences of primers were:

```
                                    (SEQ ID NO: 32)
PKS-TE-sen:     5' TgggTgTTgATgTTTCCg 3', (SEQ ID NO: 33)
PKS-TE-anti:    5' ATCTTggggTCCATTggC 3', (the same as SEQ ID NO: 13)
Scy_N_2-1:      5' gCTACgAATgggCAgACAg 3', (the same as SEQ ID NO: 14)
Scy_N_2-2:      5' CCTCggCgAAgACCTTg 3',
```

```
1,3,8-tri-(A):    5' gCAAggTCgCCgTTgTTA 3',     (the same as SEQ ID NO: 5)
and 1,3,8-tri-(B):    5' CAgTCACCgTCTTgAgAAg 3'.    (the same as SEQ ID NO: 6)
```

Figure 10:
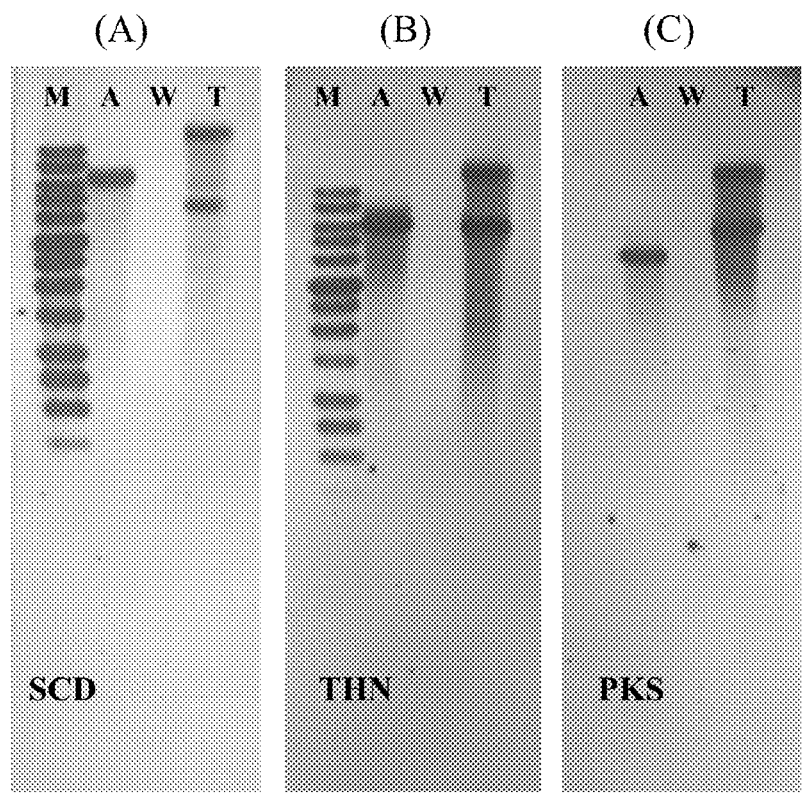

The Southern blot results are shown in FIGS. 10A-10C, (A) SCD, (B) THN, and (C) PKS, where A: *A. alternate* W: wild type *M. anisopliae* 35505 T: transformant 05-169 M: 1 kb ladder.

Example 4

Gene Expression on Transformants (1) Extraction of RNA and DNase Treatment

Total RNA of *A. alternate*, *M. anisopliae* MA35505, and *M. anisopliae* MA05-169 was extracted according to the instruction of Trizol® (Molecular Research Center, Inc). The extracted RNA was treated with 0.1 fold of 10×TURBO DNase buffer and 1 μl of TURBO DNase (Ambion) at 37° C. for 30 min, followed by the addition of 0.1 fold of TURBO inactivation reagent at room temperature for 2 min. The supernatant was collected in a 1.5 ml of tube after the centrifugation of 10,000 rpm for 1.5 min. 3 μl of the RNA was transfer to a quartz cuvette to determine the concentration.

(2) 2-Step RT-PCR

RNA of *A. alternate*, *M. anisopliae* MA35505, and *M. anisopliae* MA05-169 was reverse transcribed cDNA using Super SMART™ PCR cDNA Synthesis Kit (BD) according to the instruction.

(3) PCR Product Purification

RT-PCR products were purified with Wizard® SV Gel and PCR clean-up System (Promega) and stored at −20° C.

(4) PCR Amplification

The cDNA was using as template to perform PCR with primer pairs of PKS-TE-sen, PKS-TE-anti, Scy_N_2-1, Scy_N_2-2,1,3,8-tri-(A) and 1,3,8-tri-(B). GPD_456 primer set was designed according to the sequence of M anisopliae glyceraldehyde-3-phosphate dehydrogenase mRNA (NCBI gi|115607610) and using cDNA of *M. anisopliae* MA35505 and MA05-169 as templates for PCR amplification. In addition, GPD AA primer set was also designed according to the sequence of *A. alternata* glyceraldehyde 3-phosphate dehydrogenase (NCBI gi|131747098) and using cDNA of *A. alternata* as template for PCR amplification. The sequences of the primers were:

```
GPD-456 forward primer:
5' AggTCATCCACgACAAgTTCACCA 3',    (SEQ ID NO: 34)

GPD-456 reverse primer:
5' ACCAggAgACCAgCTTgACAAAgT 3',    (SEQ ID NO: 35)

GPD_AA_s:
5' gCCgTATCgTCTTCCgCAAT 3',        (SEQ ID NO: 36)
and

GPD_AA_a:
5' CCTTCTTggCTCCACCCTTC 3'.        (SEQ ID NO: 37)
```

Figure 11:
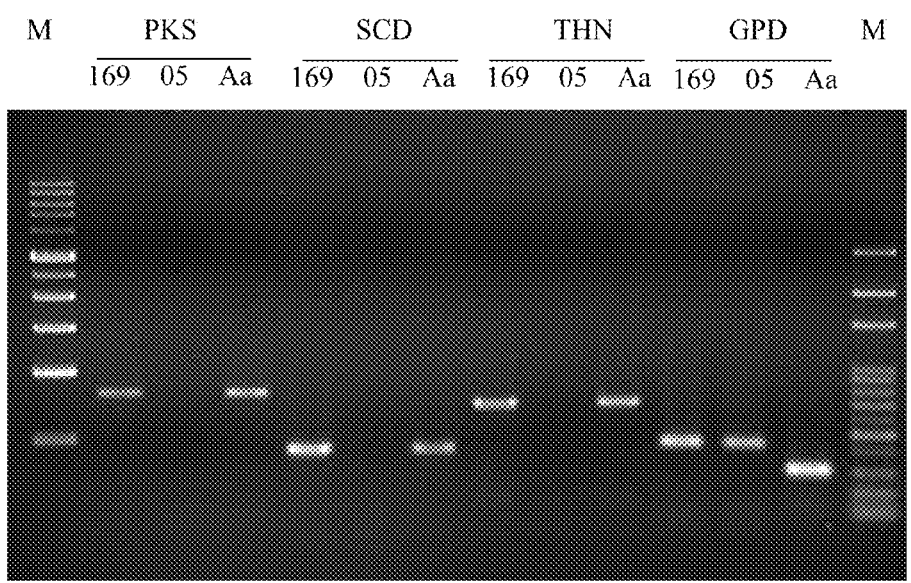

The result of RT-PCR is shown in FIG. 11, where Aa: *A. alternata* 30501, 05: *M. anisopliae* 35505, 169: transformant M anisopliae 05-169, M: DNA marker, GPD: glyceraldehyde3-phosphate dehydrogenase. Positive reactions of PKS, SCD and THN were shown in the *A. alternate* and *M. anisopliae* transformants but not the wild type *M. anisopliae*. And all the strains showed signals of *M. anisopliae* glyceraldehyde-3-phosphate dehydrogenase.

(5) Purification of Melanin

*A. alternate*, *M. anisopliae* MA35505, and *M. anisopliae* MA05-169 were cultivated in PDB at 28° C. with shaking at 220 rpm. 100 ml of the cell culture was incubated in 250 ml flasks. The mycelia were collected after filtration. The melanin was extracted and purified with strong base and strong acid according to Goncalves et al. (2005).

The purified melanin was analyzed using UV-vis, Fourier transform infrared (FT/IR) and electron paramagnetic resonance (EPR).

(6) Electron Paramagnetic Resonance Spectrophotometry, EPRS

The electron paramagnetic resonance spectrophotometry (EPRS) technique can also called as Electron Spin Resonance (ESR), which can be used to evaluate quantitatively and qualitatively the presence of free radicals. EPRS can be used to detect melanin based on the presence of endogenous stable free radicals in melanin pigments.

Figure 12:
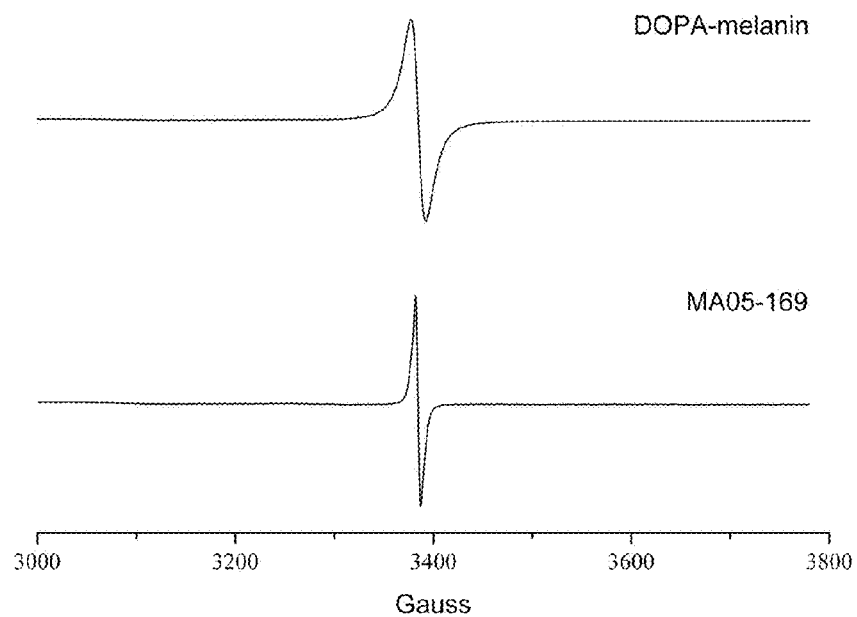

Solid melanin was studied in the experiment. Each sample was analyzed on 10 mg. EPR spectra were obtained with a Bruker EMX 10/12 spectrometer operating at modulation of 77° K, 9.48 GHz and 100 kHz (Enochs et al., 1993). The spectra were processed using Bruker WIN-EPR® software version 2.11 (Bruker, Germany) to determine the g-value (as shown in FIG. 12). g-Values of 2.00337 were found for both samples, which indicated a free electron (Motoji, 1993). Therefore melanin is postulated to have unpaired electrons.

(7) UV-Vis Spectrophotometry

The absorbance of purified melanin was determined by dissolving melanin in 0.1 m boric buffer (pH 8.0) to the concentration of 0.002% (w/v) and scanned in a UV-Vis spectrophotometer at wave length in the range of 200-500 nm. 0.1 M of boric buffer was used as blank control (Meredith and Riesz, 2004; Selvakumar et al., 2008).

Figure 13:
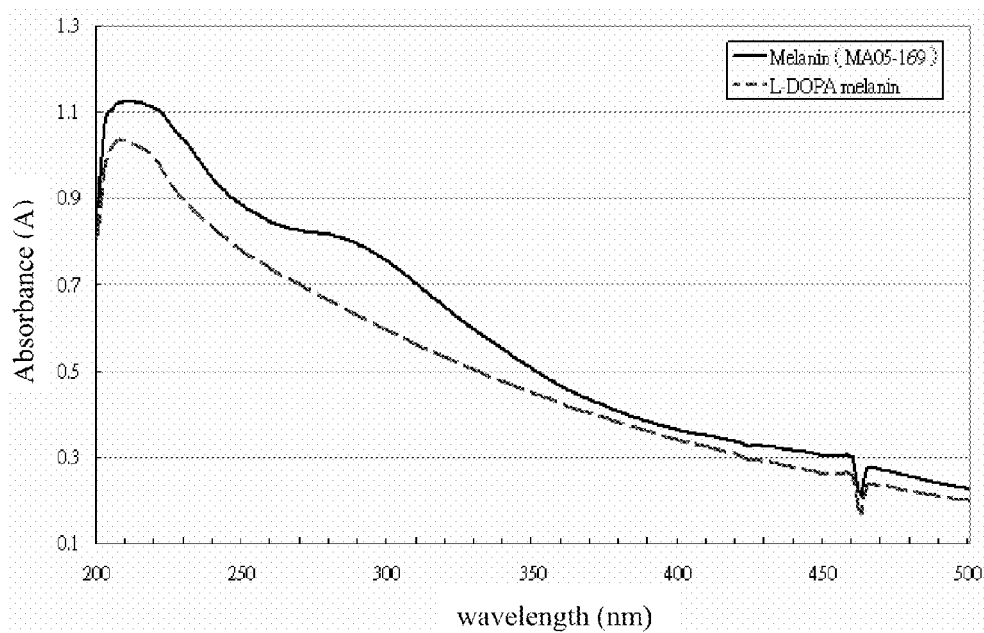
Figure 14:
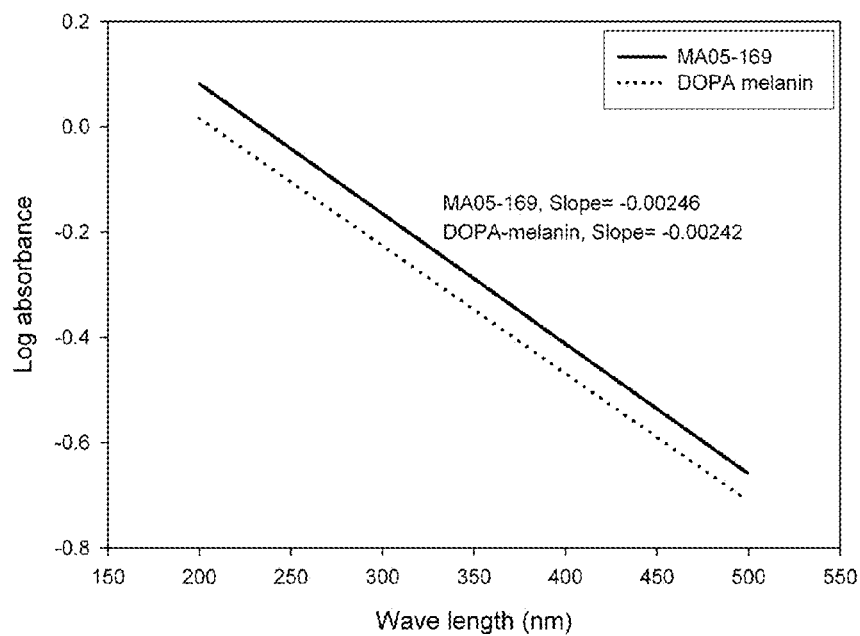

The spectra plot was shown in FIG. 13. UV-Vis absorbance spectra for standard DOPA-melanin and the 2 samples exhibited a similar pattern with a typical peak at 230 nm, followed by decreasing linearly to the basic absorbance at 500 nm. FIG. 14 showed the curves and slopes after applying linear regression to log-spectra. The slope of regression line for DOPA-melanin was −0.00209, and the slopes for the 2 samples from *M. anisopliae* MA05-169 were −0.00199 and −0.00229, which indicated similar trend for these two types of melanin. Therefore the purified melanin and the standard melanin showed the same optical characteristic in UV-Vis spectrophotometry.

(8) FT/IR Analysis

Melanin and KBr powder (Sigma) were baked at 60° C. oven for 1 h, mixed in the volume ratio of 1:19 and grounded into powder using an agate mortar and pestle. The IR spectrum was scanned in the range of 4000 nm to 400 nm with a JASCO FTIR 4100 spectrophotometer (Jasco Corporation, Tokyo, Japan) using pure KBr as blank. The spectra were analyzed with KnowItAll° (BioRad, USA) to search the functional group, and plotted with OriginPro 7.5 SR1 (USA) after the wavelength was converted to μm.

Figure 15:
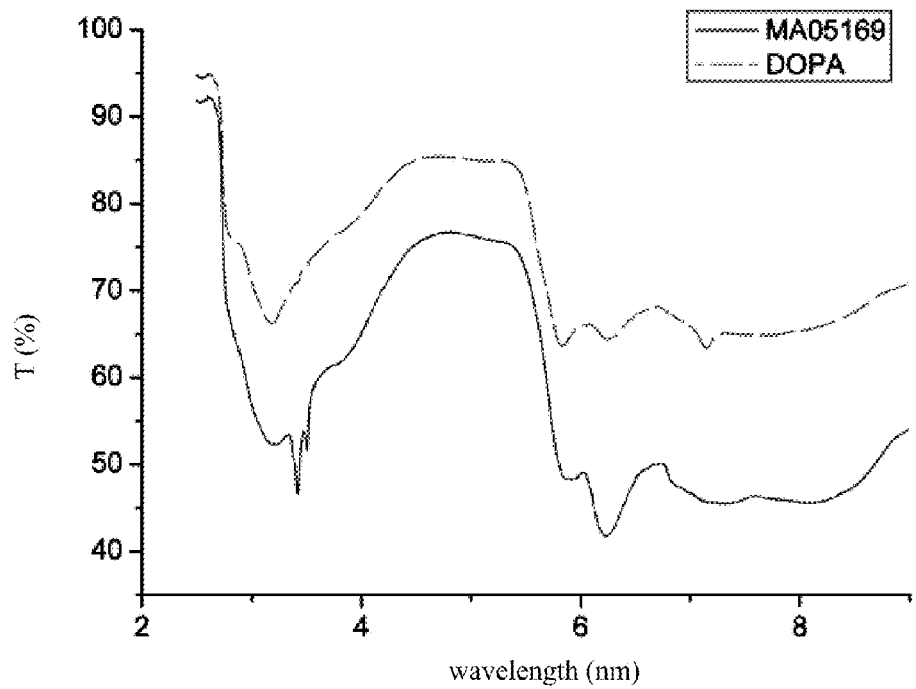
Figure 16A:
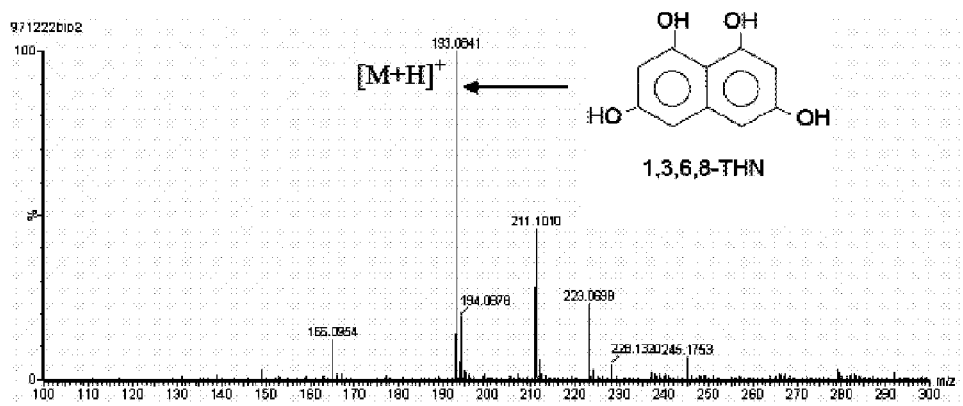
Figure 16B:
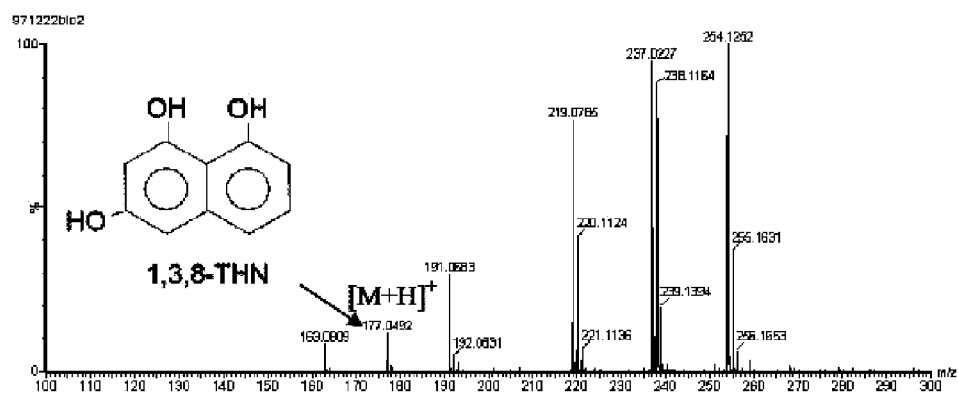
Figure 16C:
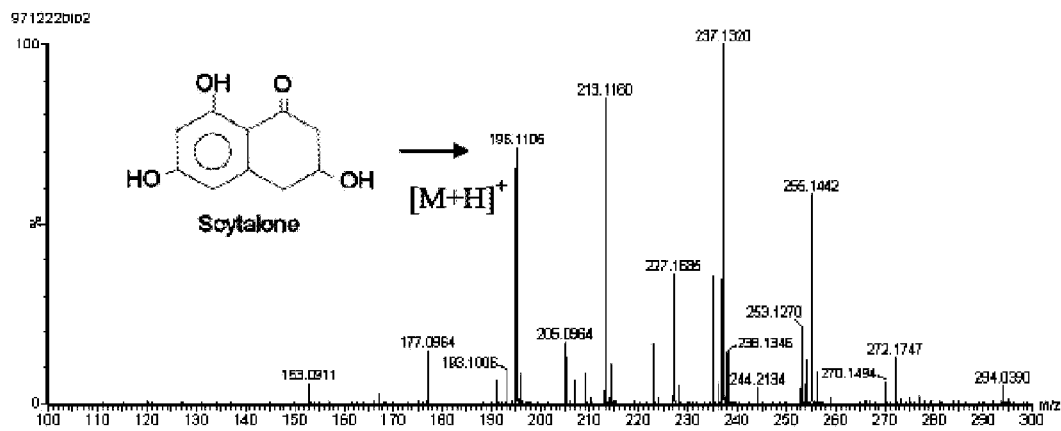
Figure 16D:
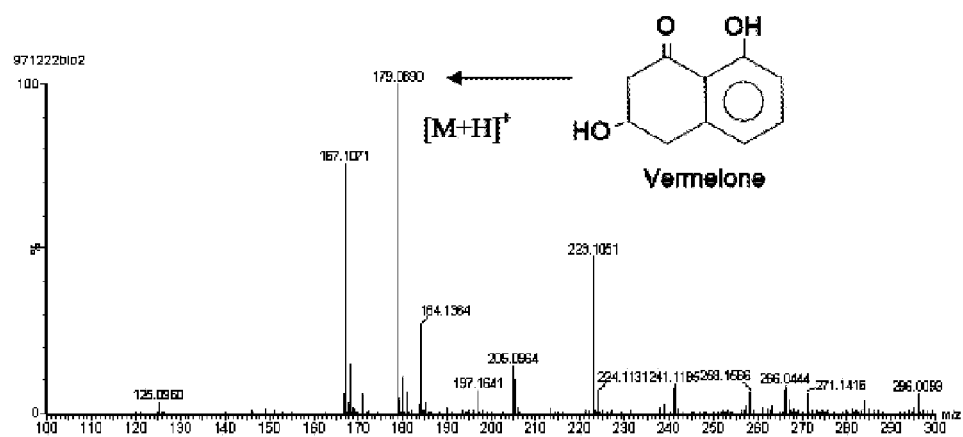
Figure 16E:
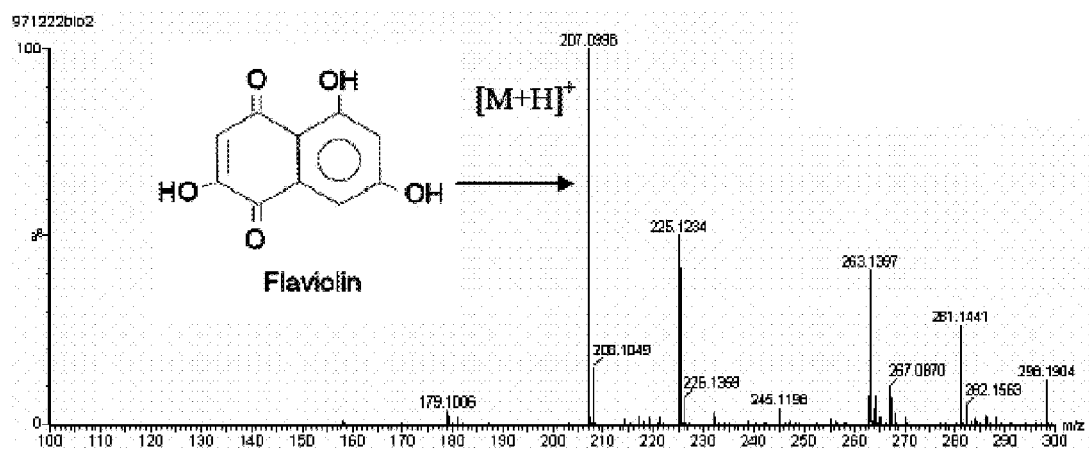
Figure 16F:
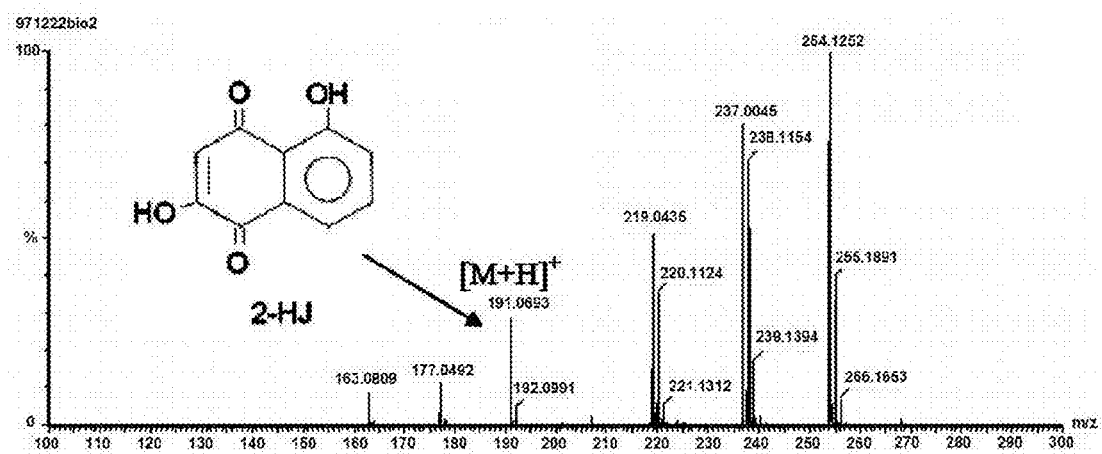
Figure 17A:
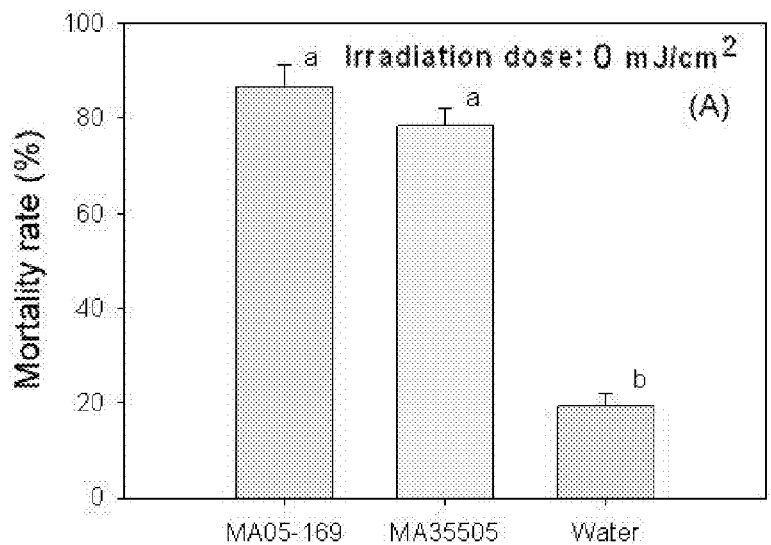
Figure 17B:
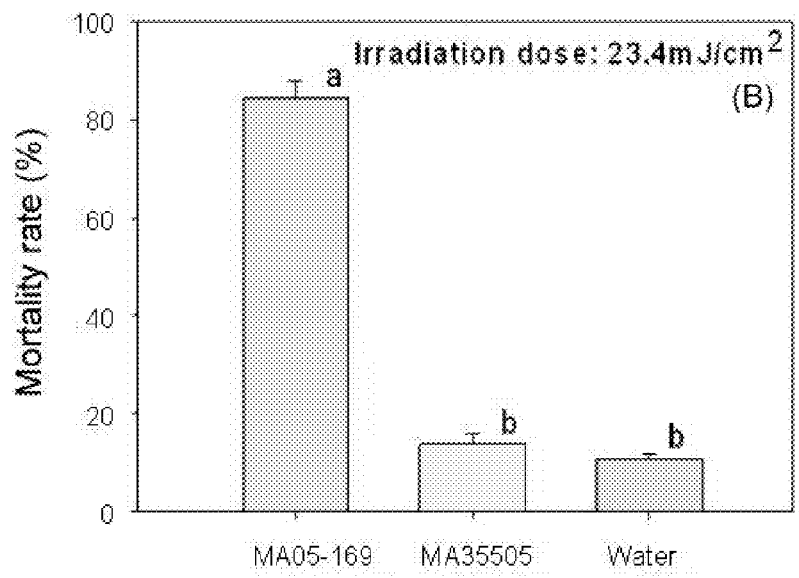
Figure 17C:
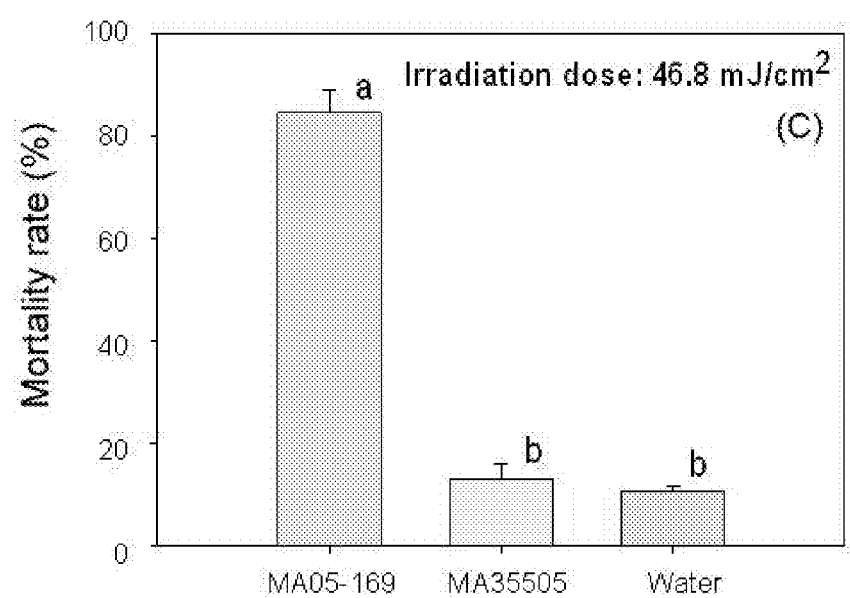
Figure 18A:
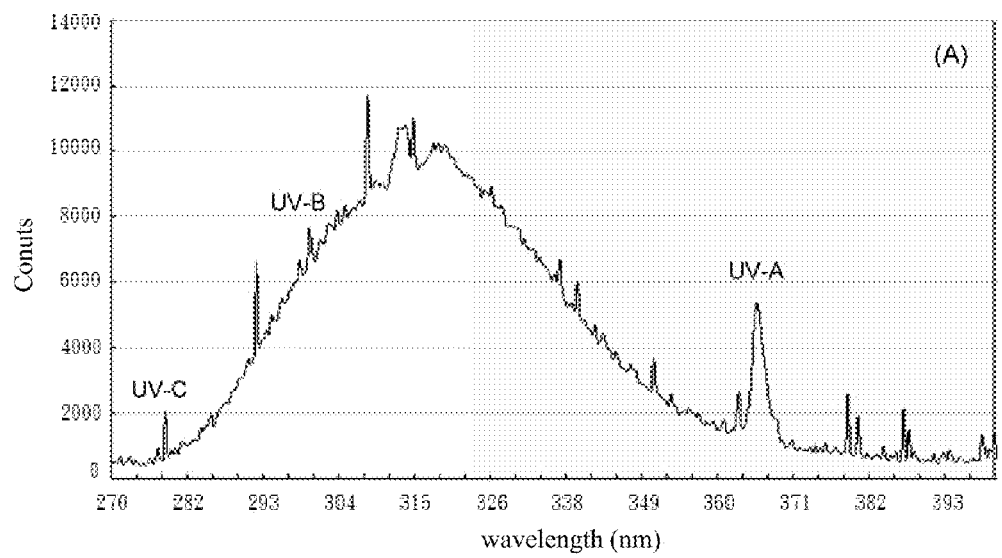
Figure 18B:
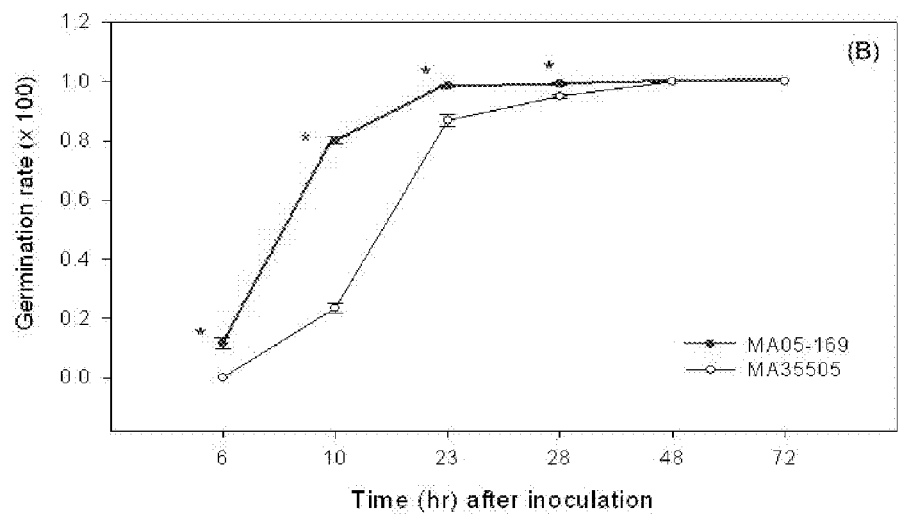
Figure 18C:
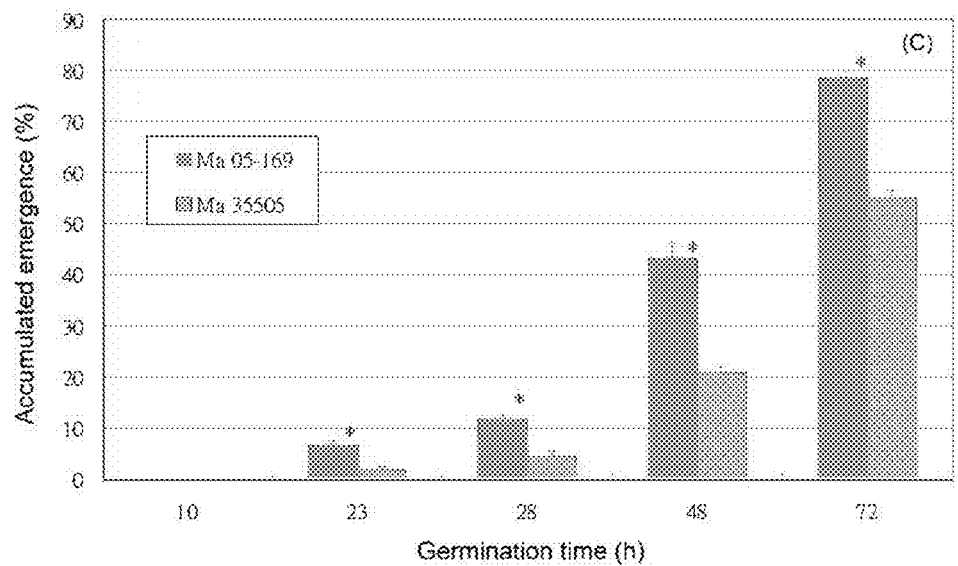
Figure 18D:
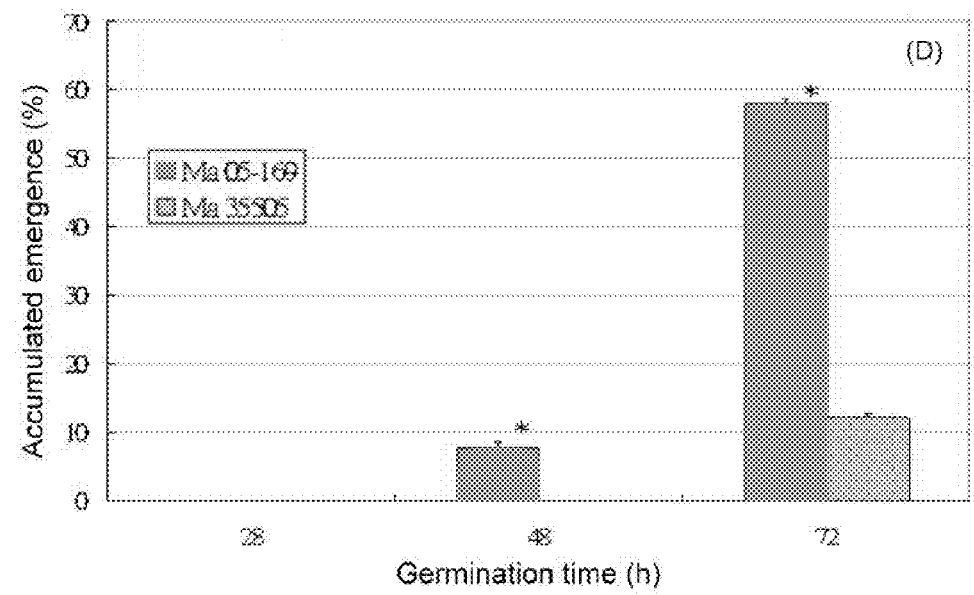

The total complex structure of melanin is not completely known. Only some monomer structures or model were provided (Kaxiras et al. 2006, Moses et al. 2006). Melanin was reported to contain carbonyl, hydroxyl and carboxyl groups. Referring to FIG. 15, the IR spectra of melanin from transformant (MA05-169) and standard DOPA-melanin were quite similar after FT/IR analysis. Both of them exhibited a peak near 3 um (~3.2 um) which might be a —NH or —OH group. An additional peak at 6 um (~5.8 um) was also shown, which could be attributed to the —C=O or double C bond (C=C) (Bonner and Duncan, 1962, Moses et al. 2006). On the other hand, an extra peak at 3.3 um was exhibited only in melanin from transformant but not in stand melanin, which might be generated by a —$CH_2$ or —$CH_3$ group.

(9) LC/MASS Analysis

Referring to FIGS. 16A to 16F, Waters CapLC, Micromass Q-TOF was used for analysis. The chromatography was carried out with a CSUN C18 column. The mobile phase was A: 95% $H_2O$, 5% acetonitrile, 1% formic acid, B: 95% acetonitrile, 5% $H_2O$, 1% formic acid, and flow rate was 9 μl/min (Greenblatt, 1986). The melanin intermediates 1,3,6,8-THN, 1,3,8-THN, Scytalone, Vermelone, Flaviolin, 2-hydroxyjuglone was confirmed by LC/MASS from the melanin secreted by transformant MA05-169 but not the wild type.

Table 2 The LC/MS analysis of melanin intermediates from M anisopliae wild type MA35505 and transformant MA05-169

| Compound | MF | MW | W | T |
|---|---|---|---|---|
| Scytalone | $C_{10}H_{10}O_4$ | 194.184 | − | + |
| Vermelone | $C_{10}H_{10}O_3$ | 178.186 | − | + |
| 1,3,6,8-Naphthalenetetrol (1,3,6,8-THN) | $C_{10}H_8O_4$ | 192.168 | − | + |
| 1,3,8-Naphthalenertriol (1,3,8-THN) | $C_{10}H_8O_3$ | 176.169 | − | + |
| 1,8-Naphthalenediol (1,8-DHN) | $C_{10}H_8O_2$ | 160.172 | − | − |
| 2-hydroxyjuglone (2-HJ) | $C_{10}H_6C_4$ | 190.15224 | − | + |
| Flaviolin (2,5,7-trihydroxy-1,4-naphthoquinone) | $C_{10}H_6O_5$ | 206.15164 | − | + |
| Jugulone | $C_{10}H_6O_3$ | 174.15284 | − | − |

MF: molecular formula; MW: molecular weight; W: wild type (MA35505); T: M. anisopliae transformant (MA05-169); +: positive; −: negative.

Example 5

Bioassay for M. Anisopliae Transformants (1) Virulence of M. Anisopliae Transformant Toward Plutella xylostella L Referring to FIG. 17A, the virulence tests were performed using 3rd instar larvae of *P. xylostella* (Diamondback moth), which was fed on 7-day rape seedlings. The conidia of *M. anisopliae* wild type MA35505 and transformant MA05-169 were washed out with 0.01% Tween 80 in the concentration of $2\times10^7$ conidia/ml after cultivated in PDA medium for 21 days. The $3^{rd}$ instar larvae of *P. xylostella* were soaked in the conidia-containing solution for 30 sec, and then dried on filters. The larvae were reared on fresh rape seedlings at 27° C. for 3 days. The mortality rates were determined by counting the living larvae. The tests were performed in triplicate employing 50 larvae for 7 times independently. The virulence tests resulted in 80% mortality rates for both groups (no significant difference) under no UV-radiation condition.

(2) Effects of UV-Radiation on the Virulence of *M. Anisopliae*

Referring to FIGS. 17B and 17C, the conidia of M anisopliae wild type MA35505 and transformant MA05-169 in the concentration of $2\times10^7$ conidia/ml were placed on Petri-dishes (5-cm in diameter) respectively and irradiated with UV in the doses of 23.4 mJ/cm and 46.8 mJ/$cm^2$ without the lids, followed by the abovementioned ways for infection, feeding and mortality rates determination. The tests were performed in triplicate employing 50 larvae for 3 times independently. The virulence test of wild type *M. anisopliae* resulted in no death of *P. xylostella*, while transformant MA05-169 still showed a mortality rate over 80% (FIG. 15). Therefore melanin-containing transformant MA05-169 showed good virulence toward *P. xylostella* even under UV-radiation condition.

(3) Germination Assay Against UV-Radiation Stress

Referring to FIGS. 18A to 18D, conidial germination assay of *M. anisopliae* wild type MA35505 and transformant MA05-169 was undertaken in UV-B radiation stress studies. Philips Ultraviolet-B TL 20W/12RS (Holland) lamps without filter were used as the source of UV-B, which emitted mostly UV-B, and some UV-C and UV-A. The distribution of spectra and energy fluence were determined with a USB2000+ Miniature Fiber Optic Spectrometer (Ocean Optics, USA) (FIG. 18A). 150-300 μl of the conidial suspension in the concentration of $10^6$-$10^7$ conidia/ml was placed evenly on Petri-dishes and irradiated with 3 UV doses (0 mJ/cm, 23.4 mJ/cm and 46.8 mJ/$cm^2$) in triplicate, and cultivated at 25° C. in the dark. Germination was observed for a period of 6, 10, 23, 28, 48 and 72 h post-inoculation under the 400× magnification. Germinated (grew over the length of conidium) and non-germinated conidia were counted in random. Random microscope fields were selected until 100 conidia had been counted. Percent germination was assessed in three random fields of view for each test.

As shown in FIGS. 18A to 18D, conidial germination rate of transformant was obvious faster than that of wild type without UV-B radiation (FIG. 18B). The germination rate of the transformant still showed significant difference from that of wild type although the germination rates of both strains were delayed by UV-B radiation. The germination rate of wild type strain at 72 h post-inoculation was 10% after irradiated at UV dose of 46.8 mJ/cm; while that of transformant was 58%, which was around 5 fold of the former. The germination rate of transformant at 48 h post-inoculation was 2-fold to wild type strain at UV dose of 23.4 mJ/cm (FIGS. 18C and 18D).

(3) Effects of Temperature on the Conidial Germination Rate of *M. Anisopliae*

The 14-day conidia of *M. anisopliae* were collected in the concentration of $10^6$ conidia/ml. 150 μl were placed in PDA plates at 10, 15, 20, 25, 30 and 35° C. incubator respectively and determined the germination rates for a period of 6, 15, 24, 39, 48, 63 and 72 h. Melanin-containing transformant MA05-169 showed significantly better germination rates than wild type no matter cultivated at high temperature (35° C.) or at low temperature (10° C.) (Table 3).

In brief, the proper temperature for conidial germination is around 20-30° C. for either wild type MA35505 or transformant MA05-169, but transformant MA05-169 showed significantly higher germination rates than wild type at the early periods of inoculation in any temperature. The germination rate of wild type strain at 30° C. after incubation for 6 h was 10%; while that of transformant was above 90%. And the germination rate of transformant at 10° C. after incubation for 15 h was around 50%; while wild type MA35505 did not germinate at that time point. The germination rates between both strains were also distinct at 15° C. after incubation for 15 h. The germination rates between both strains were not significant after incubation for 24 h at 20-30° C.; while the germination rates between both strains became indifferent only till 48 h after inoculation at 35° C. And the germination rates for transformant MA05-169 and wild type MA35505 were 97.1% and 69.5% respectively at 10° C. after 72 h.

TABLE 3

Effects of temperature on the conidial germination rate of *M. anisopliae* transformant MA05-169 and wild type MA35505

| temp | Germination rate (%) ± standard deviation (hr) | | | | | | | |
|---|---|---|---|---|---|---|---|---|
| | 6 | | 15 | | 24 | | 39 | |
| °C. | MA05-169 | MA35505 | MA05-169 | MA35505 | MA05-169 | MA35505 | MA05-169 | MA35505 |
| 10 | 0.3a ± 0.3 | 0.0a ± 0.0 | 49.5a ± 2.8 | 0.0b ± 0.0 | 43.0a ± 2.5 | 0.0b ± 0.0 | 72.5a ± 1.8 | 5.0b ± 1.1 |
| 15 | 3.2a ± 1.3 | 0.0a ± 0.0 | 90.4a ± 1.1 | 4.1b ± 0.3 | 94.7a ± 0.9 | 36.8b ± 2.9 | 99.4a ± 0.3 | 98.6a ± 0.9 |
| 20 | 66.6a ± 6.7 | 0.0b ± 0.0 | 98.7a ± 0.8 | 94.2b ± 0.8 | 100.0a ± 0.0 | 99.1a ± 0.5 | 100.0a ± 0.0 | 100.0a ± 0.0 |
| 25 | 93.5a ± 1.1 | 1.3b ± 0.8 | 100.0a ± 0.0 | 96.8a ± 0.8 | 100.0a ± 0.0 | 100.0a ± 0.0 | 100.0a ± 0.0 | 100.0a ± 0.0 |
| 30 | 94.1a ± 2.2 | 10.8b ± 3.2 | 99.7a ± 0.3 | 99.4a ± 0.6 | 100.0a ± 0.0 | 100.0a ± 0.0 | 100.0a ± 0.0 | 100.0a ± 0.0 |
| 35 | 36.9a ± 0.6 | 0.0b ± 0.0 | 96.9a ± 0.4 | 41.9b ± 3.1 | 93.9a ± 1.7 | 72.6b ± 1.3 | 99.4a ± 0.3 | 88.7b ± 0.6 |

| temp | Germination rate (%) ± standard deviation (hr) | | | | | |
|---|---|---|---|---|---|---|
| | 48 | | 63 | | 72 | |
| °C. | MA05-169 | MA35505 | MA05-169 | MA35505 | MA05-169 | MA35505 |
| 10 | 86.0a ± 2.1 | 21.8b ± 8.0 | 92.5a ± 1.7 | 27.4b ± 3.8 | 97.1a ± 1.0 | 69.5b ± 3.7 |
| 15 | 100.0a ± 0.0 | 100.0a ± 0.0 | — | — | — | — |
| 20 | 100.0a ± 0.0 | 100.0a ± 0.0 | — | — | — | — |
| 25 | 100.0a ± 0.0 | 100.0a ± 0.0 | — | — | — | — |
| 30 | 100.0a ± 0.0 | 100.0a ± 0.0 | — | — | — | — |
| 35 | 99.7a ± 0.3 | 89.2a ± 3.4 | 100.0a ± 0.0 | 83.4b ± 2.4 | 96.2a ± 3.7 | 86.5a ± 1.7 |

\* different alphabet letters represented significances between the germination rates for transformant MA05-169 and wild type MA35505 in the confidence interval of 95%.
— Not determined (4) Effects of Water Activity on the Conidial Germination Rate of *M. Anisopliae*

Glycerol was used to adjust the water activity (aw). Glycerol was added in the amounts of 0, 4, 6, 10, 12, 20, 30 and 40 g to 100 ml of PDA media. The water activities were determined with AquaLab® 3TE Water Activity Meter (Washington, USA) to be 0.996, 0.991, 0.989, 0.986, 0.977, 0.967, 0.938 and 0.895 respectively. Water activities in 0.938 and 0.895 were not included in the table since the strains could not germinate. Suspension of conidia were placed in PDA plates evenly, and cultivated at 25° C. incubator for 6, 13, 17, 24, 48 and 72 h to determine the germination rates. Melanin-containing transformant MA05-169 showed significantly higher germination rates than wild type at low water activity media. The germination rate of transformant at water activity of 0.967 after incubation for 72 h was around 40%, while wild type MA35505 could not germinate at that condition (Table 4). Therefore the tolerance toward drought was increased after transformation of melanin synthesizing genes into *M. anisopliae*.

TABLE 4

Effects of water activity ($a_w$) on the conidial germination rate of *M. anisopliae* transformant MA05-169 and wild type at different time intervals

| | Germination rate (%) ± standard deviation (hr) | | | | | |
|---|---|---|---|---|---|---|
| | 6 | | 13 | | 17 | |
| $a_w$ | MA05-169 | MA35505 | MA05-169 | MA35505 | MA05-169 | MA35505 |
| 0.996 | 16.7a ± 2.2 | 2.4b ± 0.7 | 65.8a ± 1.5 | 59.4a ± 3.4 | 87.4a ± 1.1 | 86.0a ± 1.7 |
| 0.991 | 7.1a ± 1.2 | 1.4b ± 0.8 | 58.4a ± 3.1 | 49.5a ± 1.3 | 84.7a ± 1.5 | 75.8a ± 4.5 |
| 0.989 | 6.4a ± 0.9 | 0.7b ± 0.7 | 57.3a ± 0.5 | 29.6b ± 0.9 | 80.9a ± 0.9 | 58.4b ± 2.8 |
| 0.986 | 4.1a ± 0.7 | 0.0b ± 0.0 | 34.2a ± 0.2 | 10.5b ± 0.4 | 64.1a ± 5.3 | 36.1b ± 2.2 |
| 0.977 | 4.6a ± 1.4 | 0.0b ± 0.0 | 30.2a ± 2.1 | 11.3b ± 1.3 | 61.8a ± 4.3 | 35.1b ± 3.4 |
| 0.967 | — | — | 0.0a ± 0.0 | 0.0a ± 0.0 | 0.0a ± 0.0 | 0.0a ± 0.0 |

| | Germination rate (%) ± standard deviation (hr) | | | | | |
|---|---|---|---|---|---|---|
| | 24 | | 48 | | 72 | |
| $a_w$ | MA05-169 | MA35505 | MA05-169 | MA35505 | MA05-169 | MA35505 |
| 0.996 | 95.5a* ± 0.5 | 92.8b ± 0.6 | — | — | — | — |
| 0.991 | 95.8a ± 0.5 | 90.1a ± 2.1 | — | — | — | — |
| 0.989 | 93.4a ± 0.4 | 90.5a ± 1.8 | — | — | — | — |
| 0.986 | 82.1a ± 3.4 | 84.8a ± 2.1 | — | — | — | — |
| 0.977 | 81.3a ± 0.5 | 79.3a ± 3.4 | — | — | — | — |
| 0.967 | 0.0a ± 0.0 | 0.0a ± 0.0 | 32.7a ± 1.6 | 0.0b ± 0.0 | 42.9a ± 2.6 | 4.3b ± 1.3 |

\*different alphabet letters represented significances between the germination rates for transformant MA05-169 and wild type MA35505 in the confidence interval of 95%.
$a_w$: Water activity (5) Statistics Analysis The results of the invention were subjected to statistical analysis using Statistics Package for Social Science (SPSS). Standard curve was plotted with Sigma Plot.

conclusion

Based on the outcomes of the abovementioned experiments, DHN-melanin synthesis could effectively increase the tolerance of beneficial microorganisms against UV-radiation, extreme temperature or low temperature, and drought condition. Protecting the microorganisms by synthesis of melanin by themselves is different from the traditional way of mixing the anti-UV compounds with microorganisms, which helps to increase the survival of microorganisms and shows a faster and higher infection ability to further increase the efficiency of beneficial microorganisms. The present invention can also be applied in other beneficial microorganisms and plants to effectively improve the tolerance against environmental stress.

---

What is claimed is:

1. The melanin expressing *Metarhizium anisopliae* transformant DSM 27044, which comprises a polyketide synthase (PKS) gene, a scytalone dehydratase (SCD) gene, and an 1,3,8-trihydroxynaphthalene reductase (THN) gene, and expresses melanin biosynthesis proteins of PKS, SCD and THN, wherein the PKS, SCD and THN gene were subcloned from *Alternaria alternata*.

* * * * *